(12) United States Patent
Kusleika

(10) Patent No.: US 7,887,560 B2
(45) Date of Patent: Feb. 15, 2011

(54) CATHETER WITH OCCLUDING CUFF

(75) Inventor: Richard S. Kusleika, Eden Prairie, MN (US)

(73) Assignee: ev3 Inc., Plymouth, MN (US)

( * ) Notice: Subject to any disclaimer, the term of this patent is extended or adjusted under 35 U.S.C. 154(b) by 1041 days.

(21) Appl. No.: 11/501,401

(22) Filed: Aug. 9, 2006

(65) Prior Publication Data

US 2007/0038178 A1 Feb. 15, 2007

Related U.S. Application Data

(63) Continuation of application No. 10/194,734, filed on Jul. 12, 2002, now Pat. No. 7,166,120.

(51) Int. Cl.
*A61M 29/00* (2006.01)
(52) U.S. Cl. ........................ 606/191; 606/200
(58) Field of Classification Search ................ 606/191, 606/200, 195; 604/103.03, 278, 103.05
See application file for complete search history.

(56) References Cited

U.S. PATENT DOCUMENTS

| | | | |
|---|---|---|---|
| 4,577,631 A * | 3/1986 | Kreamer ...................... 606/108 |
| 4,712,551 A * | 12/1987 | Rayhanabad ................... 604/8 |
| 4,781,682 A | 11/1988 | Patel |
| 4,921,478 A | 5/1990 | Solano et al. |
| 5,385,562 A | 1/1995 | Adams et al. |
| 5,520,698 A * | 5/1996 | Koh ........................... 606/119 |
| 5,527,292 A | 6/1996 | Adams et al. |
| 5,624,399 A * | 4/1997 | Ackerman ............. 604/103.03 |
| 5,638,813 A * | 6/1997 | Augustine .............. 128/207.15 |
| 5,643,285 A * | 7/1997 | Rowden et al. ............. 606/119 |
| 5,693,014 A * | 12/1997 | Abele et al. ............ 604/103.08 |
| 5,797,960 A * | 8/1998 | Stevens et al. .............. 606/213 |
| 5,824,044 A | 10/1998 | Quiachon et al. |
| 5,827,324 A | 10/1998 | Cassell et al. |
| 5,833,650 A * | 11/1998 | Imran ......................... 604/509 |
| 5,840,077 A * | 11/1998 | Rowden et al. ............. 606/119 |
| 5,882,334 A * | 3/1999 | Sepetka et al. ......... 604/164.08 |
| 5,916,193 A * | 6/1999 | Stevens et al. .............. 604/509 |

(Continued)

FOREIGN PATENT DOCUMENTS

EP     0 427 429 A2    5/1991

(Continued)

OTHER PUBLICATIONS

Claims for U.S. Appl. No. 08/748,066, Mazzocchi et al., Nov. 12, 1996.

(Continued)

*Primary Examiner*—Todd E Manahan
*Assistant Examiner*—Erin Colello
(74) *Attorney, Agent, or Firm*—Popovich, Wiles & O'Connell, P.A.

(57) ABSTRACT

A device, method, and system of deploying an embolic protection device at a location distal to a treatment site in a vessel of a patient. A delivery catheter is encircled by a sealing member which is expandable from a delivery configuration to a deployed configuration. The device creates a seal to prevent the flow of blood during the treatment of vascular disease. A distal protection element is delivered by the delivery catheter and deployed to filter or remove embolic debris.

20 Claims, 17 Drawing Sheets

U.S. PATENT DOCUMENTS

| | | | |
|---|---|---|---|
| 5,919,163 A * | 7/1999 | Glickman | 604/101.05 |
| 5,925,060 A * | 7/1999 | Forber | 606/191 |
| 5,937,861 A * | 8/1999 | Augustine | 128/207.15 |
| 5,941,896 A * | 8/1999 | Kerr | 606/200 |
| 6,022,340 A * | 2/2000 | Sepetka et al. | 604/500 |
| 6,029,671 A * | 2/2000 | Stevens et al. | 128/898 |
| 6,048,331 A * | 4/2000 | Tsugita et al. | 604/102.03 |
| 6,080,142 A * | 6/2000 | Sachse | 604/544 |
| 6,090,097 A * | 7/2000 | Barbut et al. | 604/511 |
| 6,139,573 A | 10/2000 | Sogard et al. | |
| 6,165,199 A * | 12/2000 | Barbut | 606/200 |
| 6,168,579 B1 * | 1/2001 | Tsugita | 604/96.01 |
| 6,206,868 B1 | 3/2001 | Parodi | |
| 6,210,408 B1 * | 4/2001 | Chandrasekaran et al. | 606/41 |
| 6,214,026 B1 * | 4/2001 | Lepak et al. | 606/200 |
| 6,231,588 B1 * | 5/2001 | Zadno-Azizi | 606/200 |
| 6,238,412 B1 * | 5/2001 | Dubrul et al. | 606/200 |
| 6,245,089 B1 | 6/2001 | Daniel et al. | |
| 6,293,952 B1 * | 9/2001 | Brosens et al. | 606/119 |
| 6,295,989 B1 | 10/2001 | Connors, III | |
| 6,312,444 B1 * | 11/2001 | Barbut | 606/200 |
| 6,315,778 B1 | 11/2001 | Gambale et al. | |
| 6,325,815 B1 | 12/2001 | Kusleika et al. | |
| 6,363,900 B1 | 4/2002 | Homi et al. | |
| 6,371,971 B1 | 4/2002 | Tsugita et al. | |
| 6,375,787 B1 | 4/2002 | Lukic | |
| 6,383,205 B1 | 5/2002 | Samson et al. | |
| 6,413,235 B1 | 7/2002 | Parodi | |
| 6,530,939 B1 * | 3/2003 | Hopkins et al. | 606/200 |
| 6,605,102 B1 | 8/2003 | Mazzocchi et al. | |
| 6,692,458 B2 * | 2/2004 | Forman et al. | 604/93.01 |
| 6,966,902 B2 * | 11/2005 | Tsugita et al. | 604/509 |
| 7,108,677 B2 * | 9/2006 | Courtney et al. | 604/96.01 |
| 2001/0011182 A1 * | 8/2001 | Dubrul et al. | 606/200 |
| 2001/0031982 A1 | 10/2001 | Peterson et al. | |
| 2001/0039411 A1 | 11/2001 | Johansson et al. | |
| 2001/0044598 A1 | 11/2001 | Parodi | |
| 2001/0047184 A1 | 11/2001 | Connors, III | |
| 2001/0049517 A1 * | 12/2001 | Zadno-Azizi et al. | 604/509 |
| 2002/0016564 A1 * | 2/2002 | Courtney et al. | 604/96.01 |
| 2002/0016565 A1 | 2/2002 | Zadno-Azizi et al. | |
| 2002/0026145 A1 * | 2/2002 | Bagaoisan et al. | 604/96.01 |
| 2002/0029031 A1 | 3/2002 | Bagaoisan et al. | |
| 2002/0052638 A1 | 5/2002 | Zadno-Azizi | |
| 2002/0120226 A1 * | 8/2002 | Beck | 604/27 |
| 2002/0121472 A1 | 9/2002 | Garner et al. | |
| 2002/0123765 A1 | 9/2002 | Sepetka et al. | |
| 2002/0165574 A1 | 11/2002 | Ressemann et al. | |
| 2002/0165598 A1 * | 11/2002 | Wahr et al. | 623/1.11 |
| 2003/0055483 A1 * | 3/2003 | Gumm | 623/1.11 |
| 2003/0199819 A1 * | 10/2003 | Beck | 604/96.01 |
| 2005/0059993 A1 * | 3/2005 | Ramzipoor et al. | 606/200 |

FOREIGN PATENT DOCUMENTS

| | | |
|---|---|---|
| EP | 0 427 429 A3 | 5/1991 |
| EP | 1 181 900 A2 | 2/2002 |
| WO | WO 96/01591 | 1/1996 |
| WO | WO 98/39046 | 9/1998 |
| WO | WO 99/08744 | 2/1999 |
| WO | WO 99/30766 | 6/1999 |
| WO | WO 9930766 A1 * | 6/1999 |
| WO | WO 99/45835 | 9/1999 |
| WO | WO 00/32266 | 6/2000 |
| WO | WO 00/56391 | 9/2000 |
| WO | WO 00/76390 | 12/2000 |
| WO | WO 01/05462 A1 | 1/2001 |
| WO | WO 01/08743 A1 | 2/2001 |
| WO | WO 01/10343 A1 | 2/2001 |
| WO | WO 0110343 A1 * | 2/2001 |
| WO | WO 01/15629 A1 | 3/2001 |
| WO | WO 01/21100 A1 | 3/2001 |
| WO | WO 01/70325 A2 | 9/2001 |
| WO | WO 01/70325 A3 | 9/2001 |
| WO | WO 01/70326 | 9/2001 |
| WO | WO 02/11627 A2 | 2/2002 |
| WO | WO 02/087677 A2 | 11/2002 |

OTHER PUBLICATIONS

Claims for U.S. Appl. No. 10/051,565, Mazzocchi et al., Jan. 18, 2002.
Claims for U.S. Appl. No. 10/051,492, Mazzocchi et al., Jan. 18, 2002.
Claims for U.S. Appl. No. 10/051,591, Mazzocchi et al., Jan. 18, 2002.
Claims for U.S. Appl. No. 10/051,537, Mazzocchi et al., Jan. 18, 2002.
Claims for U.S. Appl. No. 10/051,648, Mazzocchi et al., Jan. 18, 2002.
Claims for U.S. Appl. No. 10/060,272, Mazzocchi et al., Jan. 30, 2002.
Claims for U.S. Appl. No. 10/060,271, Kusleika et al., Jan. 30, 2002.
Claims for U.S. Appl. No. 09/824,910, Kusleika et al., Apr. 3, 2001.
Claims for U.S. Appl. No. 10/060,854, Kusleika et al., Jan. 30, 2002.
U.S. Appl. No. 10/093,572, Kusleika et al., Mar. 8, 2002.
U.S. Appl. No. 10/132,562, Anderson et al. Apr. 25, 2002.
U.S. Appl. No. 10/194,355, Adams et al., Jul. 12, 2002.
U.S. Appl. No. 10/096,624, Kusleika et al., Mar. 12, 2002.
U.S. Appl. No. 09/981,769, Oslund et al., Oct. 17, 2001.
U.S. Appl. No. 10/171,704, Adams et al., Jun. 14, 2002.
International Search Report for counterpart International application No. PCT/US03/20716 (8 pages).
US 6,348,062, 02/2002, Hopkins et al. (withdrawn)

* cited by examiner

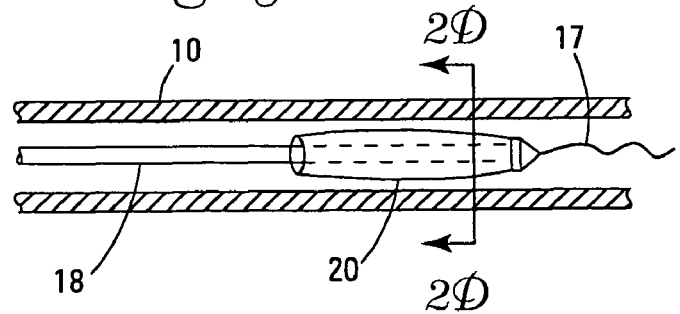
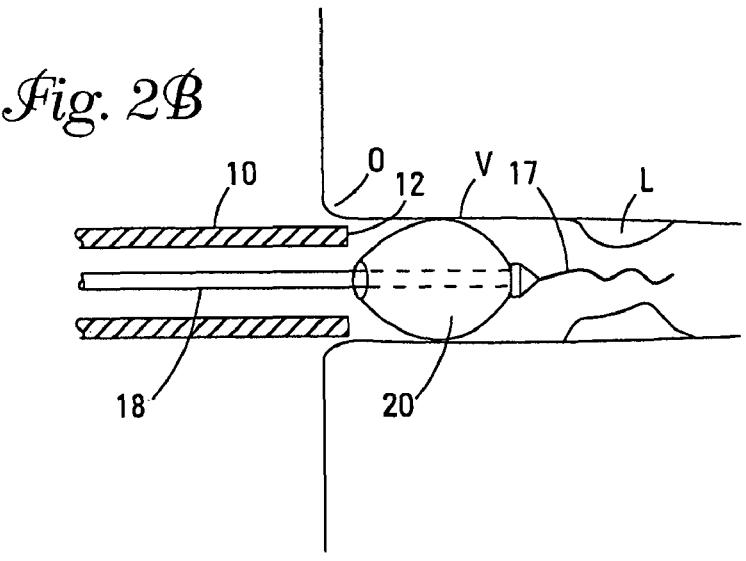
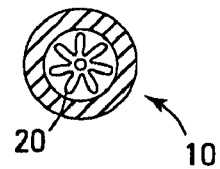
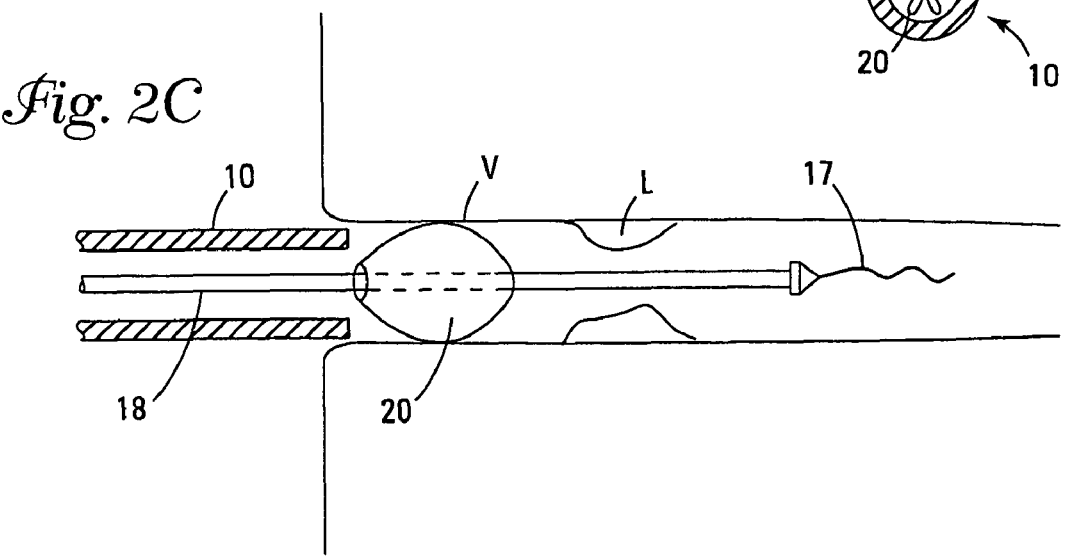

CATHETER WITH OCCLUDING CUFF

This application is a continuation of U.S. Ser. No. 10/194,734, filed Jul. 12, 2002, now U.S. Pat. No. 7,166,120 the contents of which are hereby incorporated herein by reference.

FIELD OF THE INVENTION

This invention relates to a device, a system, and a method for treating vascular disease. In particular, this invention relates to the occlusion of blood flow through a stenotic region and treatment of the region.

BACKGROUND OF THE INVENTION

Atherosclerosis or vascular disease is the leading cause of death in the world today. It is a disease of the arteries whereby deposits (plaque) build up over time in the walls of the arteries, restricting oxygenated blood flow to vital organs such as the heart, brain and other bodily tissue. A number of medical procedures have been developed to treat vascular disease such as Coronary Artery By-Pass Grafting (CABG) and Percutaneous Balloon Angioplasty (PTCA) and Stenting. These procedures are intended to restore normal flow through the arteries.

In the case of CABG, the saphenous vein is harvested from the leg and used as a conduit to by-pass blood flow from the aorta to a point distal to an obstruction in a coronary artery. After a number of years, these grafts become diseased, and treatment of the graft is needed to improve blood flow. Treatment of these degenerated grafts with PTCA or Stenting is associated with a high incidence of embolic material (vessel deposits) released distally. This can result in a no-flow condition and myocardial infarction. Similarly, treatment of carotid arteries and renal arteries by PTCA and Stenting can cause release of embolic material. In the case of the carotid artery, emboli released can result in a stroke. In the case of the renal artery, emboli release can result in the renal infarct and reduced renal function. There is a risk of embolic material being released with any balloon expansion or passage of a treatment device through a diseased section of a vessel, with undesirable results to the patient. Thus, it is highly desirable to prevent embolic material from being released during treatment of vascular disease.

The use of embolic protection devices has recently improved the outcome for treatment of these diseased grafts and arterial restrictions. There are two major approaches to embolic protection. In either case the devices are delivered to the area of treatment in the conventional means through a guide catheter or elongated sheath.

The first approach involves crossing the obstruction or diseased vessel with a deflated balloon affixed to the distal end of a hollow guidewire. The balloon segment is placed distal to the arterial segment to be treated, and the balloon is inflated to occlude flow of blood in the vessel. The PTCA or Stenting treatment is then performed over the hollow wire and any embolic material is prevented from moving beyond the distal occlusion balloon. After completion of the treatment, a suction catheter is placed into the vessel such that the distal tip is near the balloon. Suction is applied to the catheter tip and embolic material is removed from the vessel.

The second approach involves a filter mounted on a guidewire and sheathed in a delivery catheter. The sheathed filter is placed in the artery distal to the treatment site. The filter is then deployed through the sheath and expands outward adjacent the vessel wall to channel blood flow into the filter. The treatment device is then advanced over the guidewire, and any emboli generated during treatment is directed by the blood flow into the filter. The filter retains embolic material greater in size than the filter pore size. After treatment, a recovery catheter is advanced distally to a location proximal to the filter and the filter pulled proximally. The filter closes and/or the filter is drawn completely into a lumen of the retrieval catheter. The system (and captured emboli) is then withdrawn from the body.

A balloon occlusion approach can be problematic because no blood is flowing through the vessel during use of the treatment device and ischemia can develop quickly, particularly in saphenous vein grafts. The procedure must be conducted swiftly to prevent undue patient pain. There is also no assurance that all trapped emboli are removed by suction.

A filter approach can be problematic because particles smaller than the filter pore size will pass through the filter and may cause embolic events or consequence, particularly in the brain. There is also no assurance that trapped emboli will not be squeezed through the filter mesh during recovery.

Recent clinical trials show that both types of embolic protection devices reduce the occurrence of embolic events by about half in the case of saphenous vein grafts. Clinical trials currently are assessing the benefit in carotid and other arterial treatments.

Unfortunately, these approaches to embolic protection do not eliminate embolic events entirely because passage of the protection device or the catheter delivering the device across the diseased section of the vessel or lesion can dislodge embolic material prior to deployment of the device. Thus, it would be highly desirable to use a device or method that would prevent release of embolic material during passage of the embolic protection system through the vessel lesion to the deployment location. One prior art attempt to solve this problem is disclosed in U.S. Pat. No. 6,348,062 (Hopkins et al.). In this approach a PTCA balloon is inflated proximal to the treatment site (lesion) to create stasis in the vessel. Emboli liberated on lesion crossing cannot be transported distally because there is no flow. A distal protection filter is then deployed and flow in the vessel is re-established. Any emboli created during lesion crossing by the distal protection device are prevented from flowing distally. The disadvantages of this system are that a treatment balloon must be advanced into the vessel prior to creating stasis, and advancement of this balloon may liberate emboli. Further, initial treatment with a balloon is not appropriate therapy for all procedures. For example, it may be more appropriate to initially debulk a vessel using atherectomy or thrombectomy by methods commonly used in the art. Finally, it is known that even passage of a guidewire can liberate emboli, especially in saphenous vein grafts. Placement of a balloon catheter requires pre-placement of a guidewire in this prior art approach.

SUMMARY OF THE INVENTION

This invention is a device and a method that creates a seal to prevent the flow of blood during the treatment of vascular disease. A sealing cuff is disposed on a delivery catheter and is deployed to seal the vasculature. A distal protection element is delivered by the delivery catheter and deployed to filter or remove embolic debris.

In one aspect, this invention is a method of deploying an embolic protection device carried on an elongate support member at a location distal to a treatment site in a vessel of a patient. The method includes providing a delivery catheter having a distal end and a lumen sized to slideably receive the elongate support member and embolic protection device, the delivery catheter having an elongate tubular shaft encircled by a sealing member, the sealing member being expandable from a delivery configuration to a deployed configuration, introducing a guide catheter into the vessel; advancing the guide catheter through the vessel until a distal end of the guide catheter is at a desired location proximal of the treatment site, advancing the delivery catheter containing the embolic protection device through the lumen of the guide catheter until the sealing member extends from the distal end of the guide catheter, occluding the flow of blood through the vessel with the sealing member of the delivery catheter in the deployed configuration, after blood flow has been occluded advancing the embolic protection device to a location distal to the treatment site and deploying the embolic protection device. The distal end of the delivery catheter may be advanced to a position distal of the treatment site and the embolic protection device may be extended beyond the distal end of the delivery catheter. The sealing member may be slideable over a portion of the elongate tubular shaft. The step of deploying the embolic protection device also may comprise deploying a filtration device or an occlusive device. The occlusive device may be a balloon. The sealing member may be cone shaped, having an apex pointed towards the distal end of the delivery catheter, or the sealing member may be bulb shaped. The sealing member may be self-expandable.

In another aspect, this invention is a method of occluding the flow of blood in a vessel of a patient. The method includes introducing a guide catheter into the vessel, the guide catheter having an inner wall defining a lumen extending therethrough, advancing the guide catheter through the vessel until a distal end of the guide catheter is at a desired location in the vessel, introducing a sheath into the lumen of the guide catheter, the sheath having an interior surface and an exterior surface, the sheath having a sealing member adjacent the exterior surface, advancing the sheath through the lumen of the guide catheter until the sealing member extends from a distal end of the guide, and expanding the sealing member to occlude the flow of blood in the vessel.

In yet another aspect, this invention is a delivery catheter for use in delivering an embolic protection device through the lumen of a vessel to a desired location in the vessel comprising an elongate sheath having an exterior surface and a distal end, the sheath further having a lumen extending from the distal end to a location proximal of the distal end, the lumen being sized to slidingly accommodate the embolic protection device, and a sealing member connected to the elongate sheath adjacent the exterior surface, the sealing member being expandable from a delivery configuration to a deployed configuration, the sealing member in its deployed configuration being sized to fill the lumen of the vessel.

In another aspect, this invention is a delivery catheter for use in delivering an embolic protection device through the lumen of a vessel to a desired location in the vessel comprising an elongate sheath having an exterior surface and a distal end, the sheath further having a lumen extending from the distal end to a location proximal of the distal end, the lumen being sized to slidingly accommodate the embolic protection device, and means for effecting a seal between the exterior surface of the elongate sheath and the lumen of the vessel.

In another aspect, this invention is a system for occluding the flow of blood in the lumen of a vessel of a human vascular system comprising a guide catheter having proximal and distal ends and a lumen, a sheath having an interior surface and an exterior surface and being sized to be slidingly accommodated within the lumen of the guide catheter, and a sealing member connected adjacent the exterior surface of the sheath, the sealing member being expandable from a delivery configuration when the sealing member is accommodated within the lumen of the guide catheter to a deployed configuration when the sealing member is extended beyond the distal end of the guide catheter, the sealing member in its deployed configuration being sized to fill the lumen of the vessel. In the delivery configuration, the sealing member may allow passage of fluid past the sealing member and may lock onto the sheath. The sealing member may be bulb shaped. It may be slidable over the exterior surface of the sheath or fixed to the exterior surface of the sheath.

In another aspect, this invention is a system for protecting a patient from emboli released during an intravascular procedure performed at a treatment site in a vessel of a patient. This system comprises a guide catheter having proximal and distal ends and a lumen, a sheath having an interior surface defining a lumen and an exterior surface and being sized to be slidingly accommodated within the lumen of the guide catheter, a sealing member connected adjacent the exterior surface of the sheath, the sealing member being expandable from a delivery configuration when the sealing member is accommodated within the lumen of the guide catheter to a deployed configuration when the sealing member is extended beyond the distal end of the guide catheter, the sealing member in its deployed configuration being sized to fill the lumen of the vessel, and a embolic protection device sized to be delivered through the lumens of the guide catheter and sheath to a location in the vessel distal to the treatment site.

In another aspect, this invention is a method of occluding blood flow through a lumen defined by the inner wall of a vessel of a patient comprising providing a delivery catheter having a distal end and a lumen sized to slideably receive the elongate support member and embolic protection device, the delivery catheter having an elongate tubular shaft encircled by a sealing member, the sealing member being expandable from a delivery configuration to a deployed configuration, introducing a guide catheter into the vessel, advancing the guide catheter through the vessel until a distal end of the guide catheter is at a desired location proximal of the treatment site, advancing the delivery catheter containing the embolic protection device through the lumen of the guide catheter until the sealing member extends from the distal end of the guide catheter, and expanding the sealing member to seal against the wall of the vessel.

In another aspect, this invention is a method of delivering an embolic protection device carried on an elongate support member to a location distal to a treatment site in a vessel of a patient comprising providing a delivery catheter having a distal end and a lumen sized to slideably receive the elongate support member and embolic protection device, the delivery catheter having an elongate tubular shaft encircled by a sealing member, the sealing member being expandable from a delivery configuration to a deployed configuration, introducing a guide catheter into the vessel, advancing the guide catheter through the vessel until a distal end of the guide catheter is at a desired location proximal of the treatment site, advancing the delivery catheter containing the embolic protection device through the lumen of the guide catheter until the sealing member extends from the distal end of the guide catheter, occluding the flow of blood through the vessel with the sealing member of the delivery catheter in the deployed configuration, and after blood flow has been occluded, advancing the embolic protection device to the location distal to the treatment site. The step of advancing the embolic protection device may also comprise advancing the delivery catheter until the distal end of the delivery catheter is at a position distal to the treatment site and advancing the embolic protection device through the delivery catheter to a position distal to the distal end of the delivery catheter.

BRIEF DESCRIPTION OF THE DRAWINGS

FIGS. 2A to 2C and 2E to 2G are detailed illustrative views of the system of this invention, showing deployment of the delivery catheter sealing cuff and a distal protection device within a vessel, and FIG. 2D is a cross-sectional view along line 2D-2D of the sealing cuff of FIG. 2A.

DETAILED DESCRIPTION OF THE PREFERRED EMBODIMENTS

Figure 1A:
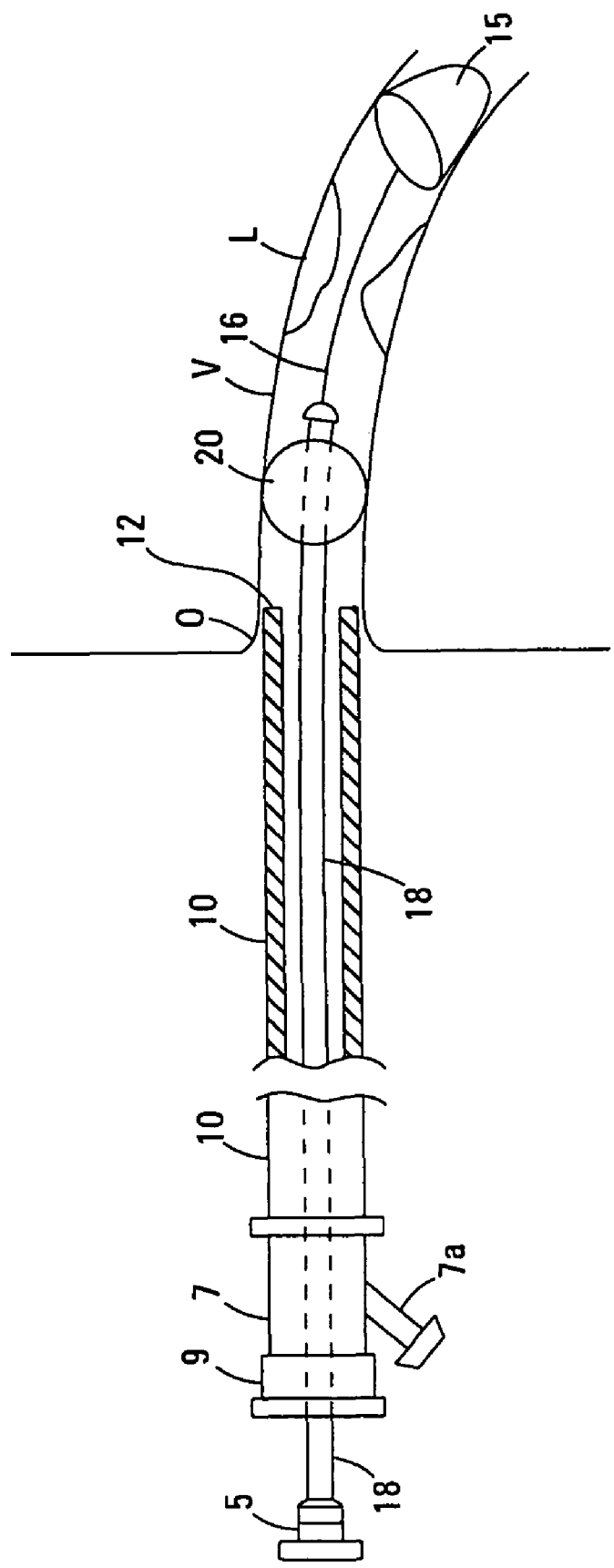
FIG. 1A is a side view in partial cross-section of the device of this invention and the delivery system used to deliver it.

The terms "distal" and "proximal" as used herein refer to the relative position of the guidewires, control wires, catheters, and sealing cuff in a lumen. "Proximal" refers to a location upstream and "distal" refers to a location downstream. Flow of blood through a lumen normally moves from the proximal to the distal portions of the device of this invention, however, the device interrupts this flow.

The Figures describe various embodiments. Elements that vary from one embodiment to another but otherwise are similar in shape, size, relative placement, or function are denoted by suffices "a", "b", "c", etc., and may be referred to in a general way by a number without its suffix.

The present invention is a device for occluding blood flow in a vessel at a location proximal to a treatment site in the vessel, thus preventing embolic material from moving distally in the vessel, prior to deployment of an embolic protection device positioned distally of the treatment site. A distal protection element is loaded into a delivery catheter. The delivery catheter is inside a guide catheter. A sealing means is disposed around the delivery catheter and seals the lumen of a vessel. The blood flow through the vessel is thus stopped. A delivery catheter, filtration device, or other distal protection device is then advanced down the vessel and across a lesion or stenosis. The seal results in little or no flow through the stenotic site when it is being crossed by the distal protection device or its delivery catheter.

The guide catheter, delivery catheter and sealing cuff, distal protection element, control wires and other components of this invention comprise biocompatible materials, and these include metals and polymeric materials. These materials can be treated to impart biocompatibility by various surface treatments, as known in the art. Desired components also may be coated with antithrombogenic materials such as heparin or materials to enhance slipperiness such as hydrophilic coatings.

The sealing cuff comprises an expandable, resilient structure, and preferably is a wire structure adjacent an impermeable membrane. The membrane may be on either or both of the inside and the outside of the wire structure or the wire structure may be embedded within the membrane.

Wire is selected on the basis of the characteristic desired, i.e., stiffness or flexibility, and the properties can depend upon both the diameter of the wire and its cross-sectional shape. The size, thickness and composition of elastic materials are selected for their ability to perform as desired as well as their biocompatibility. It is to be understood that these design elements are all within the scope of this invention.

The delivery catheter sealing cuff may comprise any material that is suitably flexible and resilient. Such may include braided, knitted, woven, or non-woven fabrics or polymeric films, alone or in combination. Suitable materials interrupt greater than about 90% of the flow in the vessel when sealing against the vessel. The delivery catheter sealing cuff may include a wire support structure which may comprise stainless steel, titanium and its alloys, cobalt-chromium-nickel-molybdenum-iron alloy (commercially available under the trade designation Elgiloy™), carbon fiber and its composites, and engineered polymers such as liquid crystal polymers, polyetheretherketone (PEEK), polyimide, polyester, nylons, and the like. A preferred shape memory metal comprises nickel and titanium and is known as "nitinol". This is commercially available in various dimensions. The sealing cuff may comprise oriented polymer films including biaxially oriented films such as those used to make angioplasty balloons, as known to one of skill in the art.

A sealing membrane may be cast onto the wire of the sealing cuff by using an elastomer that allows free diameter expansion from a smaller constrained diameter. A cast membrane may be made using a two part silicone dispersion such as that commercially available as Med-6640 from Nusil Technology, Carpinteria, Calif. Use of dipping technology is well known in the industry. Alternatively, a thin membrane may be attached to or carried by metal reinforcement by means of adhesives, sutures, thermowelding or other techniques know by those of skill in the art. Numerous polymer materials may be used such as PTFE, urethanes, polyethylene, and elastomeric materials to form a fluid impermeable layer or membrane. Suitable elastomeric materials include polyamide block copolymers (commercially available under the trade designation "PEBAX").

Where nitinol braided wire is used, the sealing cuff may be heat set to limit the expansion force against the vessel. Adequate force is needed to produce a good seal, but too much expansion force can cause drag, making it difficult to move the delivery catheter and sealing cuff through the guide catheter. Such heat set parameters are described in patent WO 96/01591 (Mazzochi et al.) and are well known in the art.

A distal protection element includes any device to be deployed in a lumen or vessel of a patient in a minimally invasive procedure. Suitable distal protection elements include occlusive devices and filtration devices. Occlusive devices include balloons, i.e., elements that are designed to expand within a vessel. Filters include, for example, those disclosed in commonly assigned, co-pending U.S. Ser. No. 10/602,271, entitled "Slideable Vascular Filter", U.S. Ser. No. 10/093,572, entitled "Distal Protection Devices Having Controllable Wire Motion", and U.S. Ser. No. 10/132,562, entitled "Vascular Protection Devices and Methods of Use", hereby incorporated herein by reference.

The distal protection element may comprise a self-expanding material. These include metals such as stainless steel, titanium and its alloys, cobalt-chromium-nickel-molybdenum-iron alloy (commercially available under the trade designation Elgiloy™), carbon fiber and its composites, and engineered polymers such as liquid crystal polymers, polyetheretherketone (PEEK), polyimide, polyester, silk, and the like. A shape memory metal is particularly suitable for those applications when it is desired for an element, such as a filter, to assume a pre-determined three-dimensional shape or for a guidewire to maintain a pre-determined curvature. A preferred shape memory metal is nitinol. For example, nitinol tubular braid can be heat set into a desired shape, compressed for delivery to a site, and then released to form the heat-set shape.

The distal protection element may also include one or more control wires. Suitable materials for the control wire include stainless steel, nitinol, alloys such as cobalt-chromium-nickel-molybdenum-iron alloy (commercially available under the trade designation Elgiloy™) or other resilient material. In a preferred embodiment, the proximal wire is a stainless steel wire in the range of 0.010 to 0.018 inch (0.025 cm to 0.046 cm) diameter, preferably 0.014 inch (0.036 cm) and preferably about 170 cm long. This wire preferably is coated with polytetrafluoroethylene (PTFE) for lubricity.

One or more radiopaque markers may be positioned at various locations on the guide seal, the guide catheter, or the distal protection element. These radiopaque markers or marker bands comprise a material that will strongly absorb X-rays and thus assist in proper placement. Suitable radiopaque materials include platinum, gold, iridium, tungsten, bismuth subcarbonate, barium sulfate, and others known to one of skill in the art.

The various embodiments of the invention will now be described in connection with the figures. It should be understood that for purposes of better describing the invention the drawings have not been made to scale. Further, some of the figures include enlarged or distorted portions for the purpose of showing features that would not otherwise be apparent.

As is known in the art, in treatment of a blood vessel, such as a saphenous vein by-pass graft, a physician first places an introducer catheter into the femoral artery. This introducer catheter is used to position a guide catheter and guidewire so that other catheters can be moved along the guidewire to a treatment site. For simplicity, the guidewire, guide catheter, and introducer catheter are not shown.

Figure 1B:
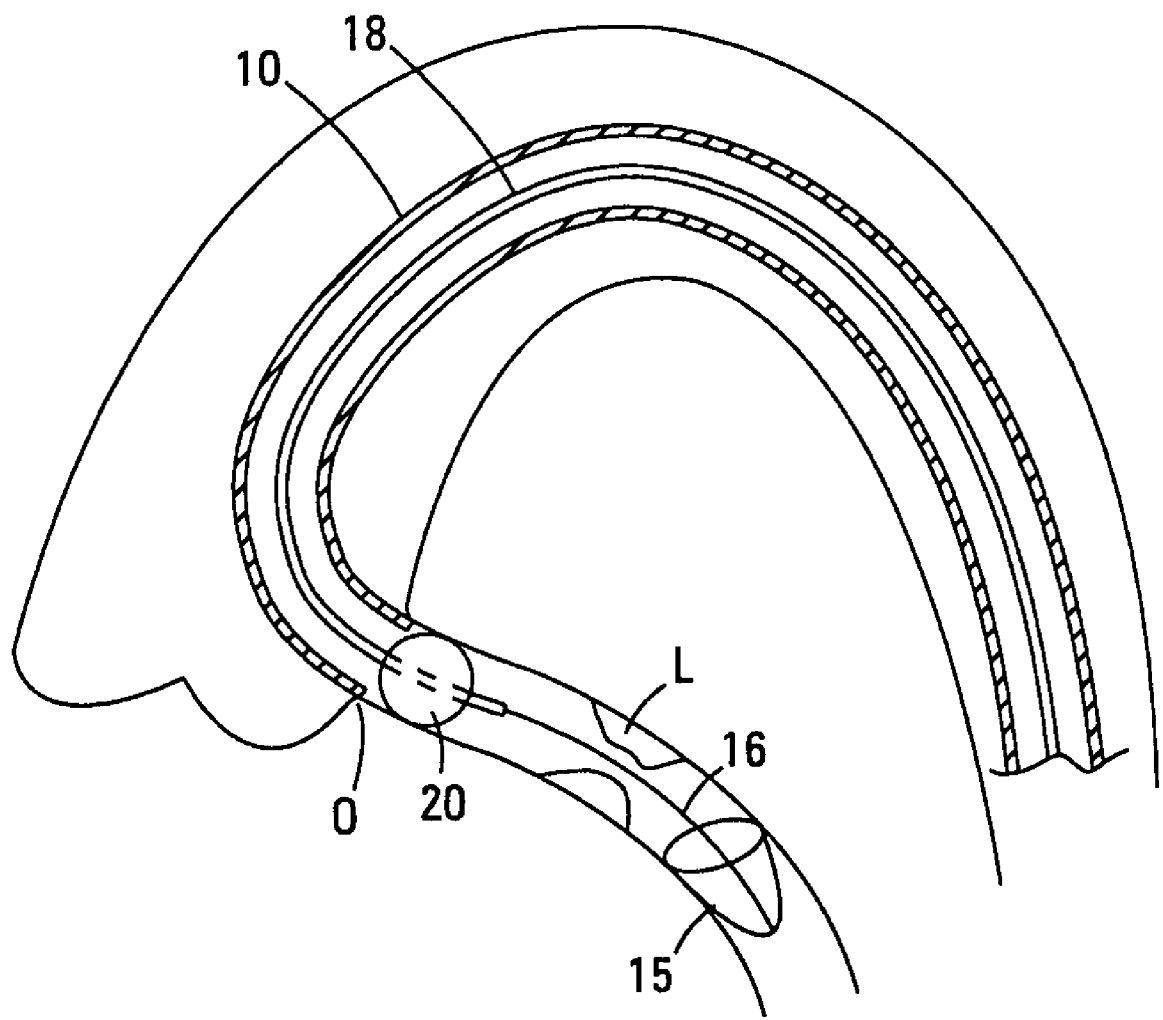
FIG. 1B is a detail view showing deployment of the apparatus within a saphenous vein graft.

The device of this invention can be understood with reference to FIGS. 1A and 1B. FIG. 1A shows a simplified linear view of the arrangement of a guide catheter 10 used in connection with a first embodiment of a delivery catheter sealing cuff 20 of the present invention. A Y connector 7 with hemostasis valve 9 is attached to the proximal end of guide catheter 10. The Y connector has optional side arm 7a. A hemostasis valve typically is attached to the proximal end of the guide catheter for ease of device passage, reduced blood loss, and to provide for injection of radiopaque contrast media through the guide. The distal end 12 of the guide catheter is shown inserted in the ostium O of a coronary vessel V which has a lesion L. The coronary vessel may be a saphenous vein graft from a previous bypass surgery. Sealing cuff 20 is slidingly disposed about delivery catheter 18, and distal protection element 15, on control wire 16, is deployed distal of lesion L. Hub or handle 5 is used to control delivery catheter 18. The sealing cuff may be coated with a slippery coating to facilitate its passage through the guide catheter and may be coated with a non-thrombogenic coating such as heparin to prevent blood clotting during periods of flow stasis. It will be understood that the catheter sealing cuff of this invention can have a variety of shapes as will be discussed in more detail hereafter.

FIG. 1B shows the guide catheter 10 and delivery catheter 18 advanced through the aortic arch. The distal ends of both catheters are within the ostium of the vessel. In FIG. 1B, sealing cuff 20 occludes the vessel and distal protection device 15 mounted on an elongate support member 16 has been advanced across the lesion.

The use of the device is as follows. The physician first places an introducer catheter into the femoral artery. A guidewire is then advanced through the femoral artery into the aorta. The guide catheter is then advanced over the guidewire until the distal tip of the guide catheter is in the ostium of the vessel. The guidewire is then removed. The delivery catheter which carries the embolic protection device of choice (typically carried on an elongate support member such as a guidewire) is then loaded into the proximal end of the guide catheter through the Y connector with the aid of an introducer, which may be tapered. The delivery catheter is advanced out the tip of the guide catheter. The sealing cuff seals against the vessel once the seal exits the guide catheter, stopping blood flow.

Once the catheter cuff has been deployed and flow through the vessel has been stopped the delivery catheter is advanced through the vessel across the lesion to a point distal to the treatment site where the embolic protection device is deployed. Any embolic material dislodged by passage of the delivery catheter and embolic protection device is prevented from flowing distally due to no flow in the vessel. Once the embolic protection device is deployed, the delivery catheter is retracted into the guide catheter and removed from the patient. At this time, if the embolic protection device is a filter, flow is re-established in the vessel and any embolic material is carried by the flow into the filter where it is captured for later removal. If the embolic protection device is an occlusive device such as a balloon, the embolic material is prevented from escaping the vessel until a suction catheter is deployed for its removal. Alternatively, the guide catheter may be used for extraction by connecting a suction source to its proximal end or to side arm 7a of the Y-connector.

Alternatively, once the guide has been seated in the vessel, a coronary guidewire can be introduced through the guide and across the treatment site. The delivery catheter with sealing cuff is advanced over the coronary guidewire, through the guide catheter, until it exits the guide, at which point flow will be stopped in the vessel due to the action of the seal. The delivery catheter can then be advanced across the treatment site in a no-flow condition. The coronary guide wire is removed and an embolic protection device advanced through the delivery catheter and deployed out the end of the delivery catheter distal to the treatment site. The delivery catheter with sealing cuff is removed from the patient, flow being thereby reestablished. Emboli liberated during lesion crossing will be carried by the reestablished flow into the filter, or in the case of an occlusive embolic protection device, can be removed by aspiration.

Figure 1C:
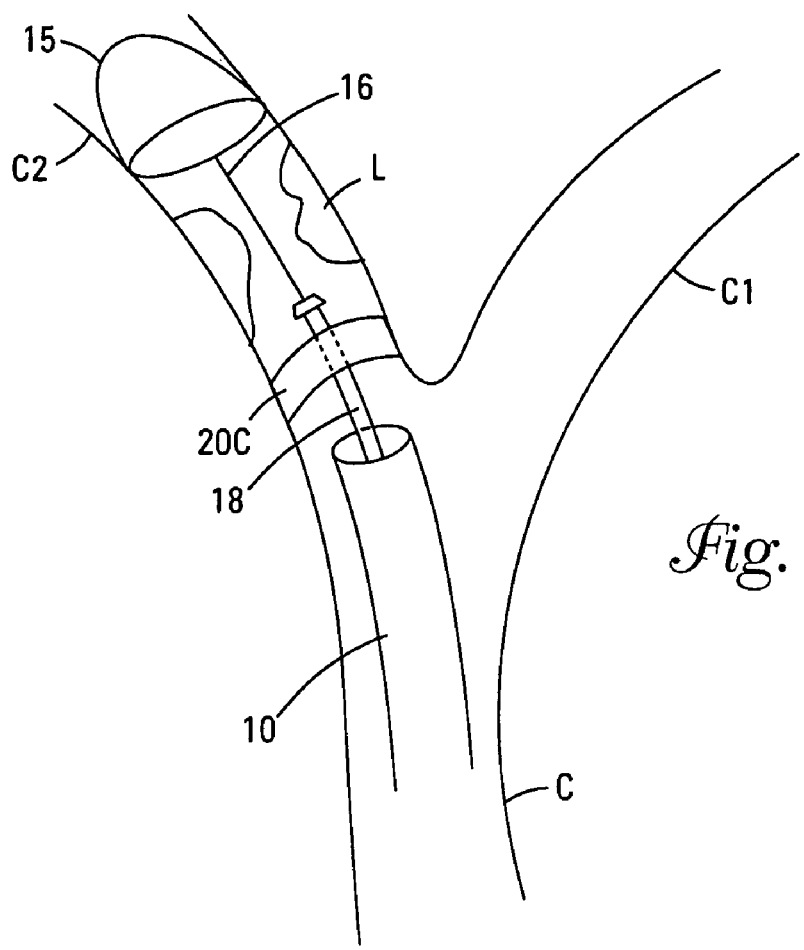
FIG. 1C is an illustrative view of deployment of the device of this invention in a carotid artery.

It is to be understood that the device of this invention could be used in any desired vessel, such as, for example, the right main coronary artery, the bracheocephalic artery, or the renal artery. FIG. 1C illustrates the use of the device of this invention in carotid artery C, having external carotid artery C1 and internal carotid artery C2. Lesion L is present in the internal carotid artery. The distal sealing portion of a sealing cuff 20c is shown deployed beyond the distal end of catheter 10 and distal protection element 15, on control wire 16, is deployed distal of lesion L. The sealing cuff is proximal to the lesion. The sealing cuff is able to seal the internal carotid artery and then the lesion can be treated as described above.

Figure 1D:
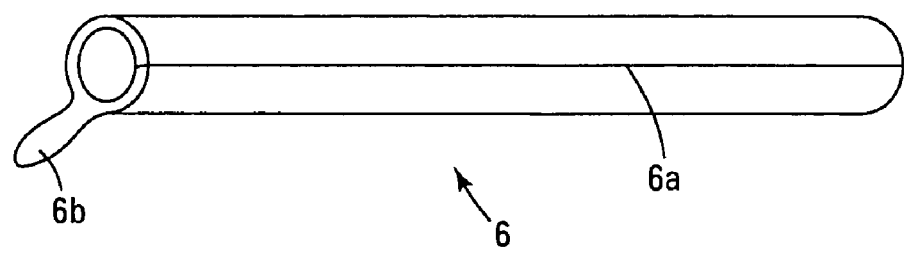
FIG. 1D is a perspective view of an introducer used to load the guide catheter into the system.

FIG. 1D illustrates introducer 6, which is used to load the delivery catheter 18 with sealing cuff 20 into Y connector 7. Introducer 6 is a cylinder having longitudinal slit 6a and tab 6b. The delivery catheter is front loaded into introducer 6. Introducer 6 is then positioned in the Y connector until it abuts the proximal end of the guide catheter. Then the delivery catheter is pushed into the guide catheter and the introducer is withdrawn from the Y connector. The introducer is then pulled sideways off the delivery catheter (i.e., the delivery catheter passes through the slit). Tab 6b facilitates gripping the introducer, pulling it out of the Y connector, and pulling it off the delivery catheter. Optionally the introducer could be provided with a larger proximal diameter, tapered to meet the distal diameter, to facilitate front loading the catheter with the sealing cuff into the introducer.

Figure 2E:
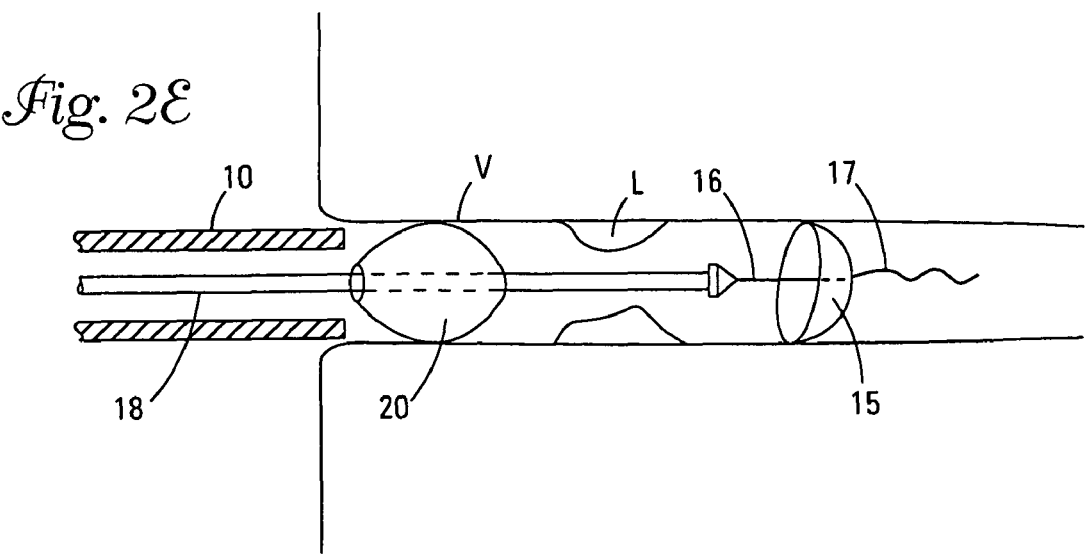

FIGS. 2A to 2C and 2E to 2G illustrate in a simplified manner the stepwise deployment of the sealing cuff in a coronary artery. FIG. 2A shows sealing cuff 20 on delivery catheter 18 inside guide catheter 10. Floppy tip 17 of the embolic protection device (not shown) extends from delivery catheter 18. The sealing cuff is constructed so that it does not act like a plunger as the delivery catheter is moved down the guide catheter. This would result in air being drawn into the proximal end of the guide catheter. FIG. 2D illustrates a sealing cuff with a wrinkled shape while in the guide catheter which permits fluid flow across the cuff as the delivery catheter is advanced. The sealing cuff is also constructed to lock onto the delivery catheter while in the guide catheter so as to remain at the delivery catheter tip during advancement through the guide catheter.

Figure 2F:
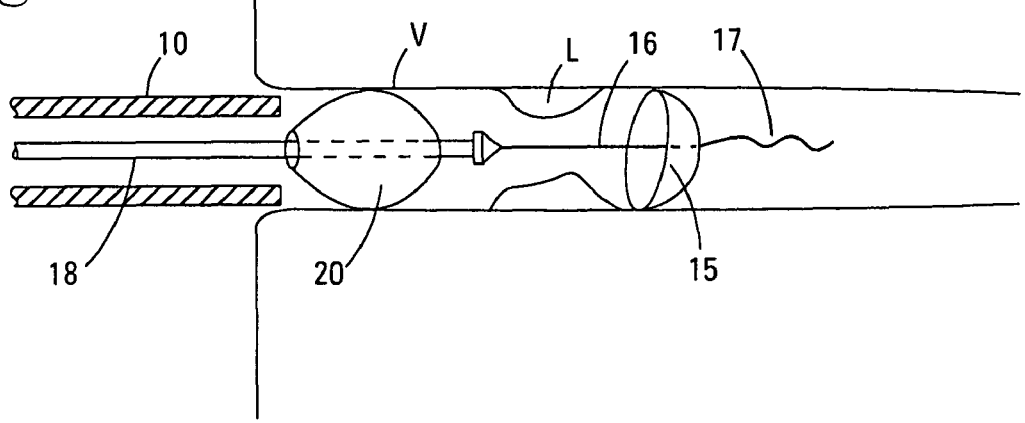
Figure 2G:
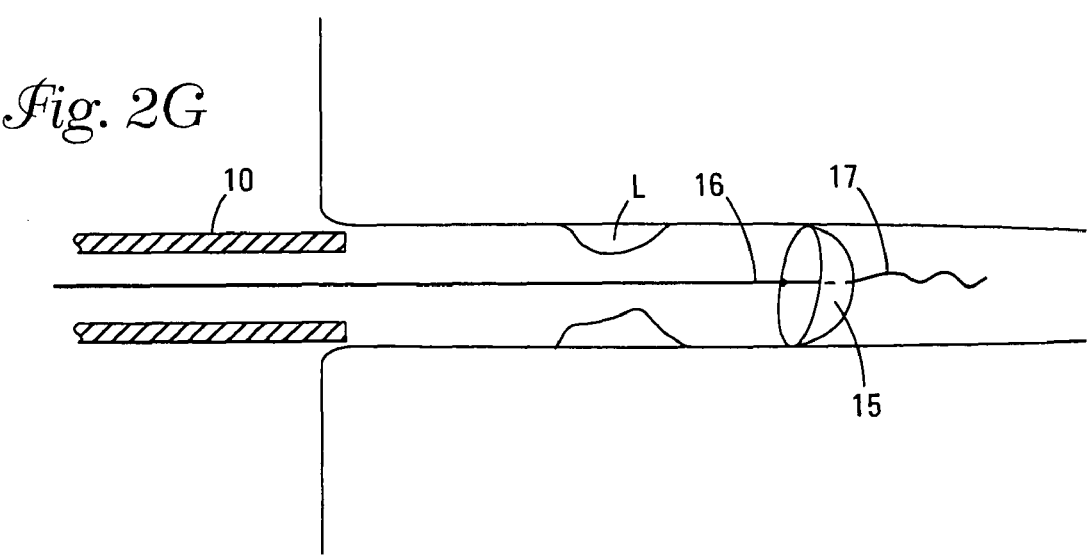

FIG. 2B shows that the distal end of guide catheter 10 is in position at the desired ostium O. Delivery catheter 18 has been advanced through the guide catheter to a desired position adjacent the distal end of guide catheter 10. Sealing cuff 20 has a bulb shape when expanded within the lumen of vessel V and acts to stop blood flow. Sealing cuff 20 is now slideable along the delivery catheter. FIG. 2C shows the advance of the delivery catheter across the lesion, while sealing cuff 20 remains deployed and proximal to the lesion. FIG. 2E shows deployment of the distal protection element 15 on its elongate support member 16 at a location distal of the lesion. In FIG. 2F, the delivery catheter is withdrawn proximally, while the sealing cuff maintains its position, and the distal protection element is distal of the lesion. In FIG. 2G, the delivery catheter has been withdrawn proximally out of the guide catheter, flow has been re-established, and debris liberated during crossing of the lesion collected by filter 15. At this point a treatment device of choice (i.e., a balloon, atherectomy device, stent) or a combination thereof may be advanced over elongate support member 16 to the treatment site. When the procedure is finished, the embolic protection device is withdrawn into the guide catheter or a retrieval catheter and both are removed from the patient. Alternatively, a separate retrieval sheath may be used to recover the embolic protection device.

Various alternative embodiments of delivery catheter sealing cuffs and particular features thereof are described in connection with FIGS. 3A to 20C.

Figure 3A:
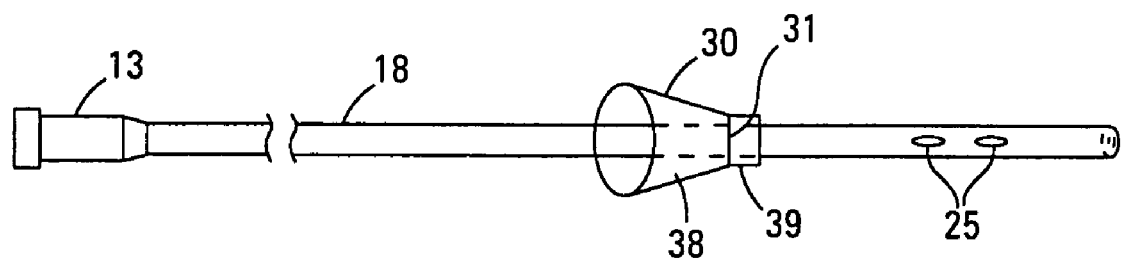
FIGS. 3A and 3B are perspective views of various embodiment of the device of this invention.
Figure 3B:
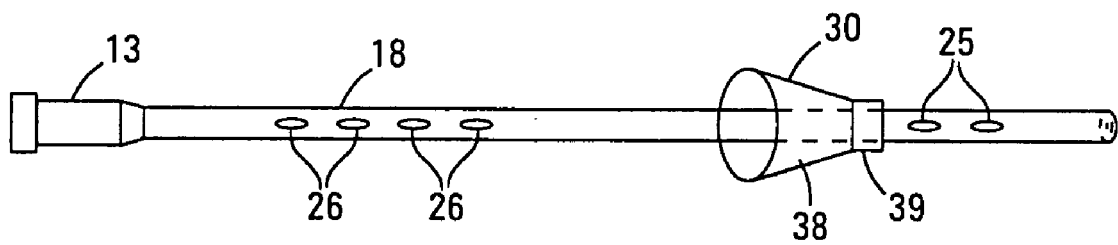
Figure 5:
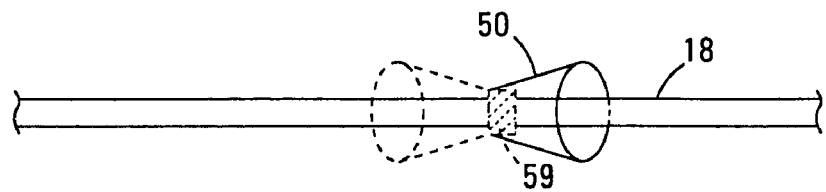
FIG. 5 is a perspective view of an alternate embodiment of the device of this invention that has an everting sealing cuff.

FIG. 3A illustrates a delivery catheter 18 provided with a conically shaped sealing cuff 30. The conical shape provides certain advantages. It makes use of flow pressure to help maintain the seal. Additionally, this seal will easily advance down a vessel in a distal direction. When pulled proximally this seal will evert to facilitate its withdrawal into the guide catheter as shown in FIG. 5. At the proximal end is luer lock hub 13. Typically, the sealing cuff is placed 1 cm to 25 cm proximal to the distal end of the catheter. Sealing cuff 30 comprises a flexible polymer membrane 38 attached at its distal end 31 to element 39. Element 39 may be fixedly attached to the external surface of delivery catheter 18 or may be slideable over the delivery catheter. Element 39 may be formed integrally with the polymer membrane. Alternatively, sealing cuff 30 is comprised of stainless steel or nitinol braid and covered with a fluid impermeable membrane such as silicone or polytetrafluoroethylene (PTFE). The delivery catheter is provided with one or more vent holes 25, shown distal to sealing cuff 30 in FIG. 3A. In FIG. 3B, additional vent holes 26 are added proximal to the sealing cuff. Vent holes prevent air from being drawn into the guide catheter as the delivery catheter with sealing cuff moves distally in the guide catheter. Delivery catheter 18 may be provided with one or more guidewire ports or lumens to facilitate guidewire exchange and tracking as described in commonly assigned and copending U.S. patent applications Ser. Nos. 09/981,769 and 10/171,704, which are hereby incorporated herein by reference in their entirety.

Figure 4A:
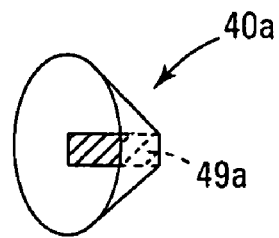
FIGS. 4A to 4E are schematic views of various embodiments of the device of this invention.
Figure 4B:
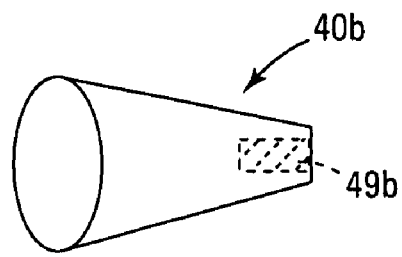
Figure 4C:
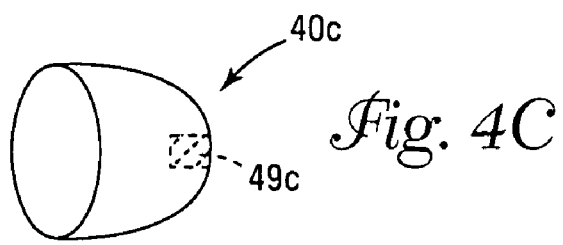
Figure 4D:
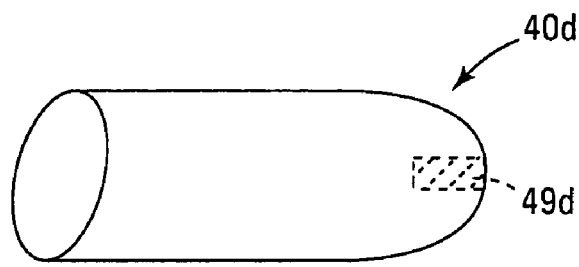
Figure 4E:
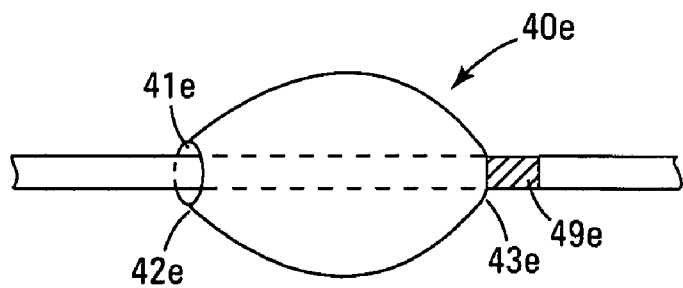

FIGS. 4A to 4E show various configurations of delivery catheter sealing cuffs. Sealing cuff 40a in FIG. 4A has a truncated conical shape and sliding element 49a (shown in outline) is inside the cone. Sealing cuff 40b in FIG. 4B is an elongated cone and sliding element 49b is inside the cone. This should be contrasted with sealing cuff 30 shown in FIGS. 3A and 3B, in which element 39 is outside, or distal, to the cone. The sealing cuff 40c of FIG. 4C, as shown with sliding element 49c, is tulip shaped and has a circular cross-section. The sealing cuff 40d of FIG. 4D, as shown with sliding element 49d, is cylindrical. A particularly advantageous sealing cuff 40e, as illustrated with sliding element 49e, is shown in FIG. 4E. Cuff 40e has an ovoid configuration with opening 41e that has a sliding fit over the delivery catheter. Opening 41e is sufficiently large relative to the delivery catheter such that when sealing cuff 40e is compressed, air or fluid within the sealing cuff's interior space is expressed through opening 41e and around the delivery catheter. This aspect of seal 40e allows the seal to be primed, reducing the chance of air introduction into the vasculature by means of air entrapment within the seal. Further, proximal and distal ends of the sealing cuff, 42e and 43e, respectively, are tapered so as to facilitate sliding of the seal through vessels and over atheroma, implants, or obstructions, without hanging up on an implant, or scraping off loose deposits from the vessel wall.

FIG. 5 illustrates a sealing cuff that everts. Sealing cuff 50 has been everted compared to sealing cuff 30 shown in FIG. 3A. The sealing cuff is shown with element 59 and is everted when the delivery catheter is pulled proximally. When the sealing cuff contacts the distal end of the guide catheter further movement of the delivery catheter in a proximal direction results in eversion of the sealing cuff.

Figure 6A:
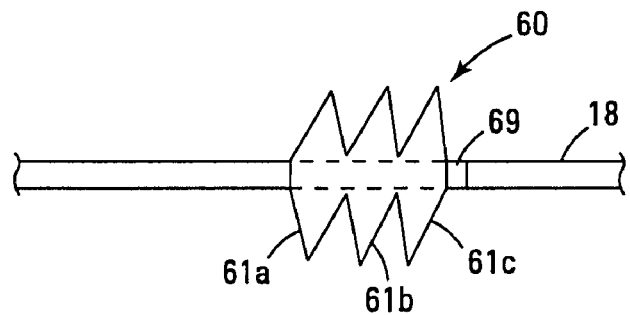
FIGS. 6A to 6C are side views of further embodiments of the device of this invention having a bellows configuration.
Figure 6B:
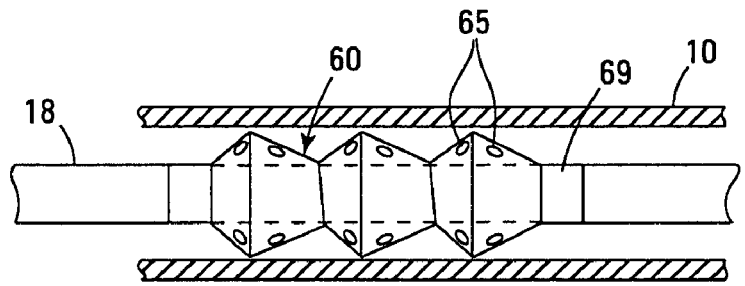
Figure 6C:
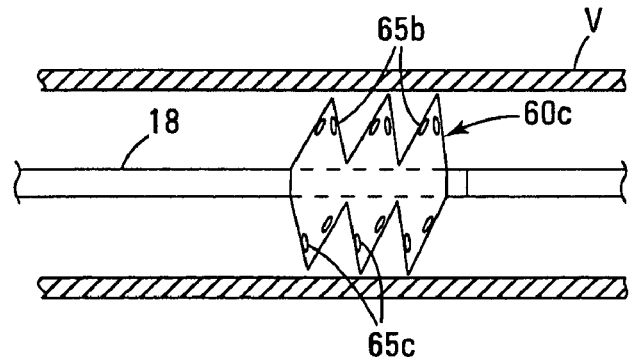

FIGS. 6A to 6C show a bellows structure for sealing cuff 60, attached to delivery catheter 18 by fixed element 69. Sealing cuff 60 comprises pleated segments 61a, 61b, and 61c, though it is understood that any number of pleated segments could be used. Sealing cuff 60 is shown in its compressed deployed configuration in FIG. 6A, and in its elongated delivery configuration in FIG. 6B. As shown in FIG. 6B, holes 65 may be provided in the bellows structure, which allow the sealing cuff to vent as it is advanced through guide catheter 10. FIG. 6C illustrates the compressed deployed configuration of sealing cuff 60c within a vessel V. Sealing cuff 60c is similar to cuff 60 of FIGS. 6A and 6B, but it has holes 65b that can be aligned with one another as shown in the top pleats of the bellows and holes 65c that can be offset as shown in the bottom pleats of the bellows. Offset holes are preferred, as sufficient blood is allowed through to vent the sealing cuff during its advancement through the guide catheter in its expanded configuration while sealing the vessel with substantially no leakage in its contracted deployed configuration due to the tortuous flow path of the offset holes.

Figure 7A:
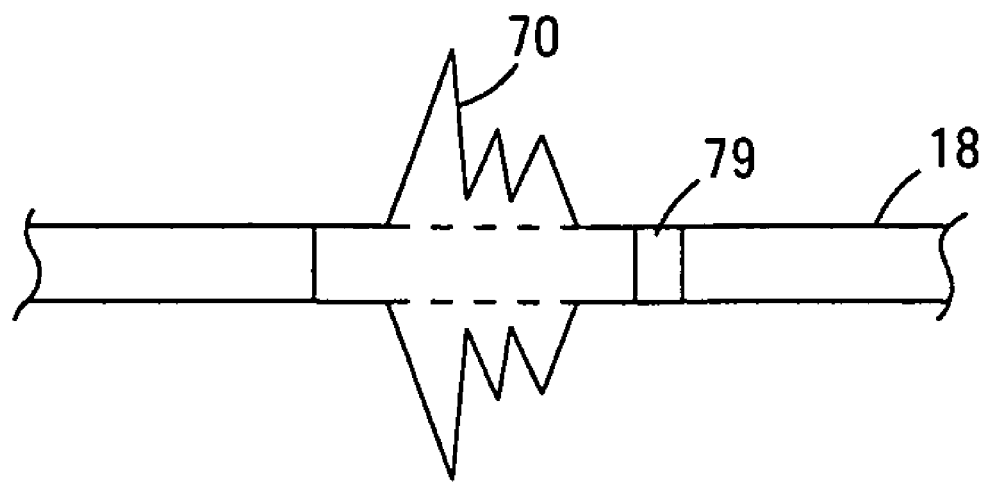
FIG. 7A is a side view of an alternate bellows configuration and FIG. 7B is an end view of the device of FIG. 7A.
Figure 7B:
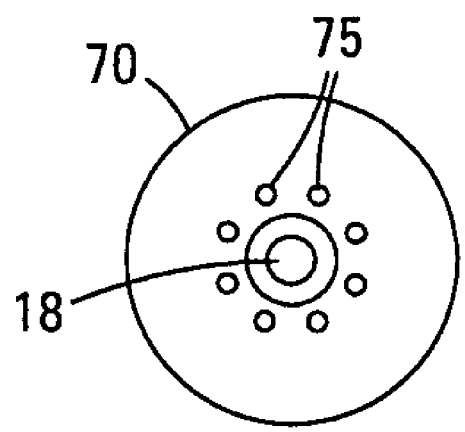

FIG. 7A illustrates a tapered bellows 70, which permits the sealing cuff to fit a greater number of vessels, and element 79. FIG. 7B shows that the bellows are provided with vent holes 75, shown in annular configuration. To effect sealing to flow during bellows contraction, adjacent bellows pleats have radially offset holes such that holes in one pleat abut against solid bellows membrane in an adjacent pleat.

Figure 8A:
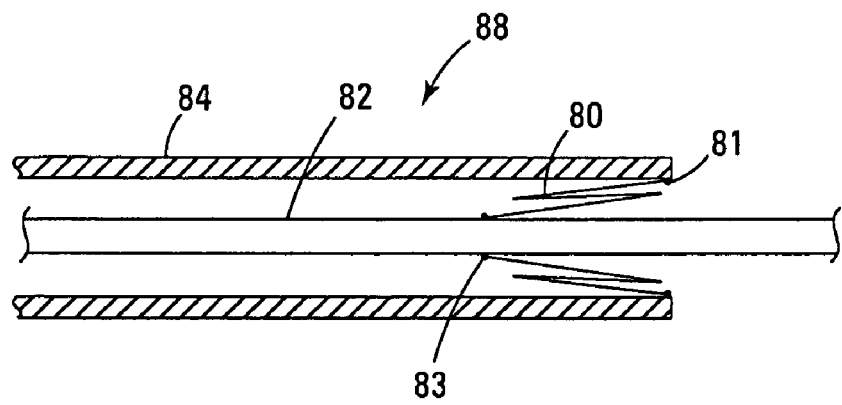
FIGS. 8A to 8C are side views of further alternate embodiments of the device of this invention.
Figure 8B:
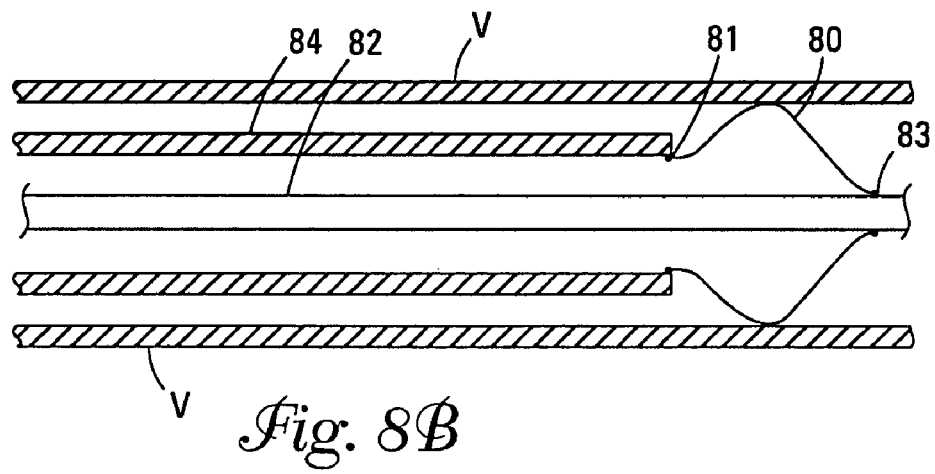
Figure 8C:
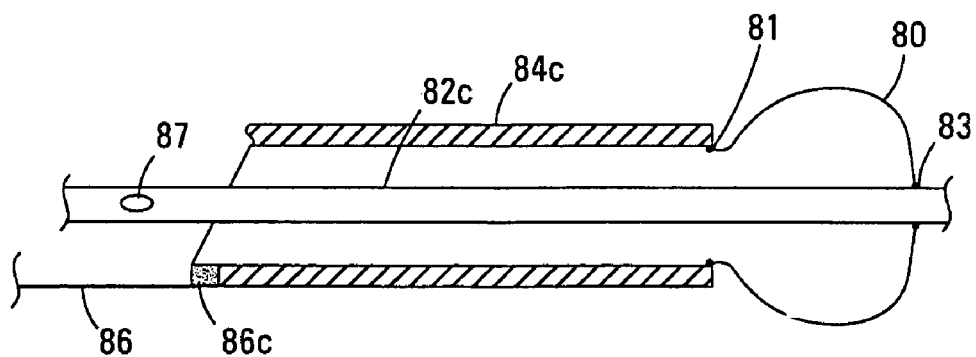

FIGS. 8A to 8C show an alternate embodiment of this invention. Delivery catheter 88 comprises an inner tube 82 which is moveable with respect to an outer tube 84. A membrane 80 is attached around the circumference of the outer tube near its distal end 81 and to an outer circumference of the inner tube at a location 83. The sealing cuff is comprised of membrane 80. In use the delivery catheter is advanced through the guide catheter by pushing the outer tube distally. During advancement the membrane is contained within an annular space between the inner and outer tubes. The membrane is deployed at a desired location by pushing the inner tube in a distal direction. This draws the membrane out of the annular space. The membrane is biased to self-expand and seal the vessel as shown in FIG. 8B. This can be accomplished by means of wires embedded in the membrane as described in connection with FIG. 14. The inner tube crosses the lesion while flow is interrupted and a distal protection device is then advanced through the inner tube and deployed distally of the lesion. The membrane may be made sufficiently long to facilitate distal advancement of the inner tube relative to the outer tube. Then either the inner or outer tube can be pulled proximally to withdraw the delivery catheter. In either case the membrane/seal will collapse against the inner tube or within the annular space.

If it is desired that the delivery catheter of FIGS. 8A and 8B is a rapid exchange delivery catheter having one or more ports, then the outer tube must be comparatively short and the proximal end of outer tube 84c will be connected at point 86c to wire 86, as shown in FIG. 8C. Inner tube 82c is provided with port 87.

Figure 9A:
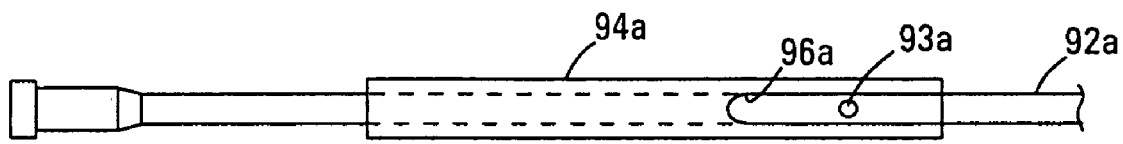
FIG. 9A is a side view of a further alternate embodiment of the device of this invention and FIGS. 9B and 9C are partial side views of variations to the embodiment of FIG. 9A.
Figure 9B:
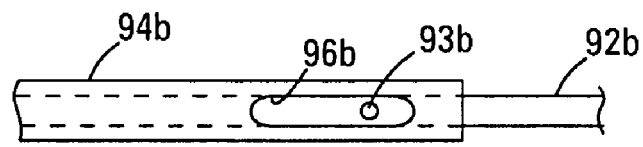
Figure 9C:
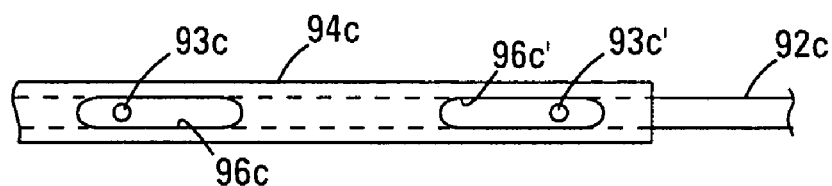

Alternatively, the outer tube can be provided with one or more slots to provide access to the guidewire ports. With this type of delivery catheter, an inner tube slides relative to an outer tube. FIGS. 9A to 9C show three different embodiments of such a slotted tube design with inner tubes 92a, 92b, and 92c moveable with respect to outer tubes 94a, 94b, and 94c, respectively. The outer tubes have slots 96a and 96b and the inner tubes are provided with ports 93a and 93b, respectively, in FIGS. 9A and 9B. FIG. 9C shows an embodiment wherein the outer tube has two slots 96c and 96c' able to access ports 93c and 93c', respectively.

Figure 10:
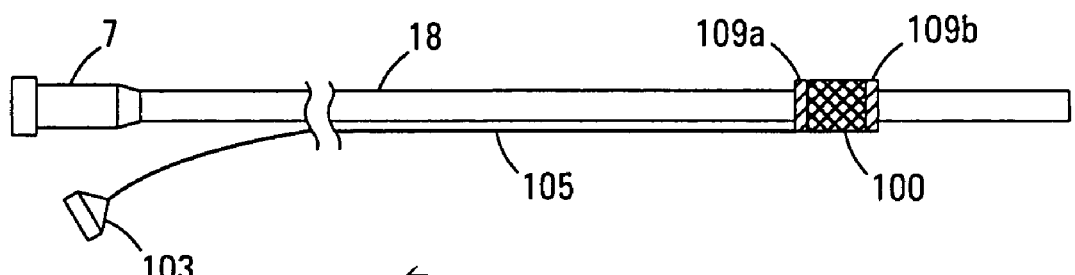
FIG. 10 is a side view and FIGS. 11 and 12 are perspective views of further alternate embodiments of the device of this invention having an external actuating mechanism.
Figure 11:
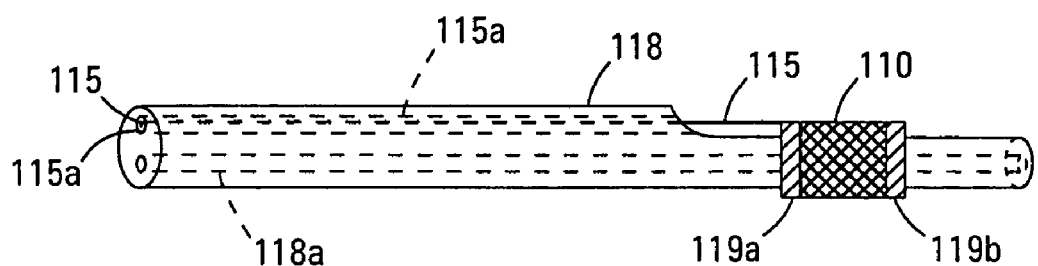
Figure 12:
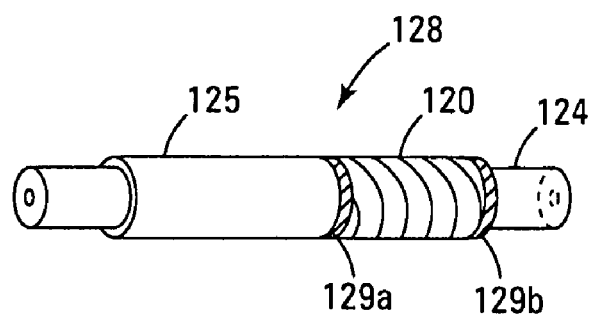

FIGS. 10 to 12 illustrate embodiments in which the sealing cuff is actuated with a control means. In FIG. 10, sealing cuff 100 is disposed about delivery catheter 18. The sealing cuff comprises braid and it is biased to collapse. The braid may be covered with an elastic membrane or may be sufficiently dense so as to substantially impede blood flow. Sealing cuff 100 is affixed to catheter 18 by a fixed element 109b at its distal end and by sliding element 109a at its proximal end. The fixed element is a marker band and the sliding element is at least two marker bands with wires from the braid held between them by means of adhesives, welding, or the like. A control wire 105 is also attached to the proximal end of sealing cuff 100. Control wire 105 is operably connected to handle 103. By moving control wire 105, the sealing cuff can be expanded or contracted. In use, delivery catheter 18 with sealing cuff 100 is advanced through the guide catheter with sealing cuff contracted. The delivery catheter with cuff is advanced out the guide catheter and into the vessel where the sealing cuff is expanded by means of control wire 105. Flow is thereby stopped in the vessel. Catheter 18 with expanded sealing cuff 100 can be advanced through the vessel, with sealing cuff sliding against vessel wall, until distal end of the delivery catheter crosses a treatment region. Any emboli liberated during crossing of the treatment region or sliding of the sealing cuff will not flow distally due to flow stasis in the vessel. An embolic protection device can next be advanced through the delivery catheter and deployed distal to the treatment site. Sealing cuff 100 is now contracted using control handle 103 and control wire 105 and delivery catheter 18 is removed.

FIG. 11 shows a variation similar to that of FIG. 10 but in this embodiment control wire 115 is contained within a lumen 115a (shown by the dashed lines) of delivery catheter 118. Lumen 118a of the delivery catheter is also shown by dashed lines. The control wire attaches to sealing cuff 110 at slider element 119a at the proximal end. At the seal's distal end is fixed element 119b. The fixed element is positioned from 1 to 10 cm from the distal end of the delivery catheter. Use of the device shown in FIG. 11 is similar to that described above for FIG. 10.

Rotational actuation can also be used, as shown in FIG. 12, in which sealing cuff 120 is affixed to rotatable outer shell 125 of delivery catheter 128 by proximal element 129*a*. The sealing cuff comprises helical wires covered with a polymeric membrane. The rotatable outer shell is mounted on inner shell 124 of delivery catheter 128. The distal end of sealing cuff 120 is affixed to the inner shell by distal element 129*b*. When the outer shell is rotated in a clockwise direction relative to the inner shell, the sealing cuff expands. Use of the device shown in FIG. 12 is similar to that described above for FIG. 10.

In most of the previously described embodiments, the sealing cuff is fixed at some location with respect to the delivery catheter. This can be an advantage because the location of the cuff is precisely controllable by manipulation of the delivery catheter. However, a fixed cuff can be a disadvantage in some clinical situations, such as when the desired location of the sealing cuff from the distal end of the delivery catheter cannot be accurately anticipated. This relative location can depend in large part on the condition of the vessel which varies from procedure to procedure. Thus, in some situations it is desirable to have a sealing cuff that is slideable on the delivery catheter. Such a sealing cuff can be deployed in a desired location in the vessel and after deployment of the seal, the delivery catheter can be advanced across the lesion without moving the sealing cuff. The embodiments disclosed in FIGS. 13-19 are examples of delivery catheters having slideable sealing cuffs.

Figure 13:
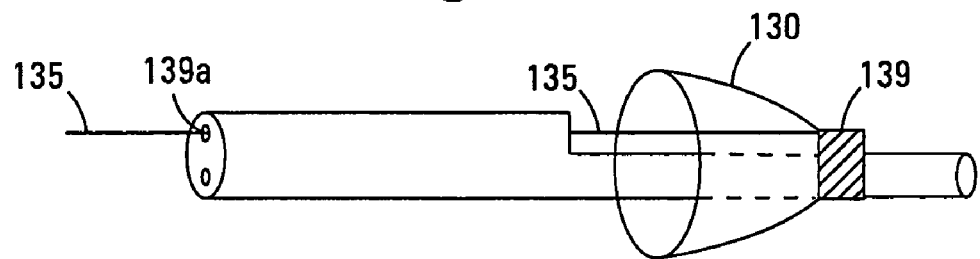
FIG. 13 is a perspective view of an alternate embodiment of the device of this invention having a control wire.

FIG. 13 illustrates an embodiment in which a control rod or wire is used to control the location and placement of the sealing cuff. Sealing cuff 130 is affixed to a sliding element 139 which slides over the delivery catheter. A control rod 135 extends through lumen 139*a* in the delivery catheter and is connected to sliding element 139. The control rod 135 is designed to be accessible outside the patient. In use, the control wire is stabilized against axial movement during advancement of the delivery catheter by shaping the wire in a serpentine pattern to create a frictional lock in the lumen, by using a clip at the proximal end of the catheter, or by the operator holding the wire with his hands. This maintains the position of the sealing cuff at or near the distal end of the delivery catheter. The cuff can be deployed by moving the control wire distally and advancing the cuff out of the guide. The cuff can be repositioned by moving the control wire proximally or distally. Proximal cuff repositioning, if desired, is best achieved by designs incorporating sealing cuffs as shown in FIG. 4E.

Figure 14A:
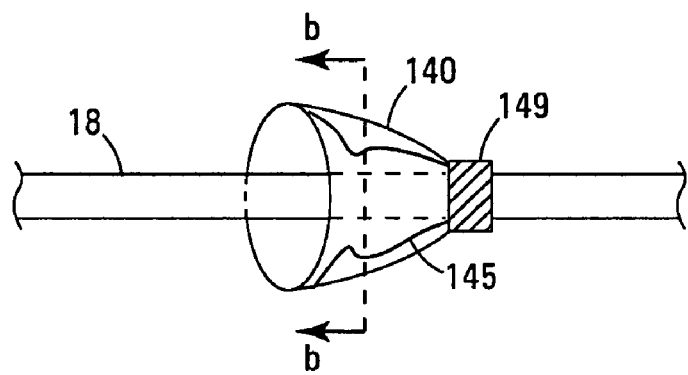
FIG. 14A is a side view of a further embodiment of the delivery catheter sealing cuff of this invention having shaped reinforcing wires in the deployed configuration.
Figure 14B:
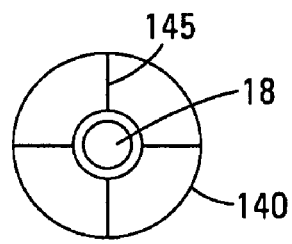
FIG. 14B is an end view showing the position of the reinforcing wires.
Figure 14C:
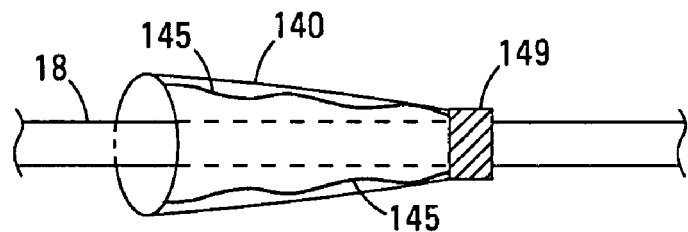
FIG. 14C is a side view of the sealing cuff in a delivery or removal configuration.

FIGS. 14A to 14C disclose another embodiment of a slideable sealing cuff which can be maintained at a fixed location during advancement of the delivery catheter. In this embodiment sealing cuff 140 has shaped reinforcing elements 145 which may be wire of sufficient strength and rigidity such as metals (stainless steel or nitinol) and engineering polymers (polyethylene terephthalate (PET), nylon, liquid crystal polymers), elastomeric polymers such as urethanes, and polyamide block copolymers (such as those commercially available under the trade designation "PEBAX"). The shaped reinforcing elements may have various shapes in cross-section. The wires are embedded within a polymeric membrane. Sealing cuff 140 is attached to delivery catheter 18 by sliding element 149. FIG. 14A shows sealing cuff 140 in its deployed configuration. FIG. 14B is a cross-sectional view along line b-b and illustrates that the reinforcing wires can be symmetrically arranged. In FIG. 14C, the sealing cuff is collapsed within the guide catheter, and the reinforcing wires 145 contact the catheter shaft to produce a friction lock. Once the delivery catheter is advanced so that the sealing cuff is past the distal end of the guide catheter the sealing cuff self-expands and is deployed in the vessel. The frictional lock of the reinforcing wires is released and the delivery catheter can be further advanced without disturbing the sealing cuff. After the delivery catheter has crossed the lesion and the embolic protection device has been delivered and deployed distal to the lesion the delivery catheter is withdrawn proximally. Delivery catheter 18 has an enlarged tip (See FIG. 17) which engages sliding element 149 and pulls the sealing cuff proximally towards the guide catheter. When the open end of the sealing cuff contacts the distal end of the guide catheter the sealing cuff everts and is drawn into the guide catheter. A feature of this design is that the frictional lock can be initially effected at any location on the delivery catheter shaft. Further, although not shown in FIGS. 14A to 14C the delivery catheter shaft can be dimensionally enlarged or reduced over certain portions of its length. This enables the sealing cuff to be more easily stabilized at areas of increased dimension or, alternatively, not be stabilized at all over certain areas of the catheter shaft with reduced dimensions.

Figure 15A:
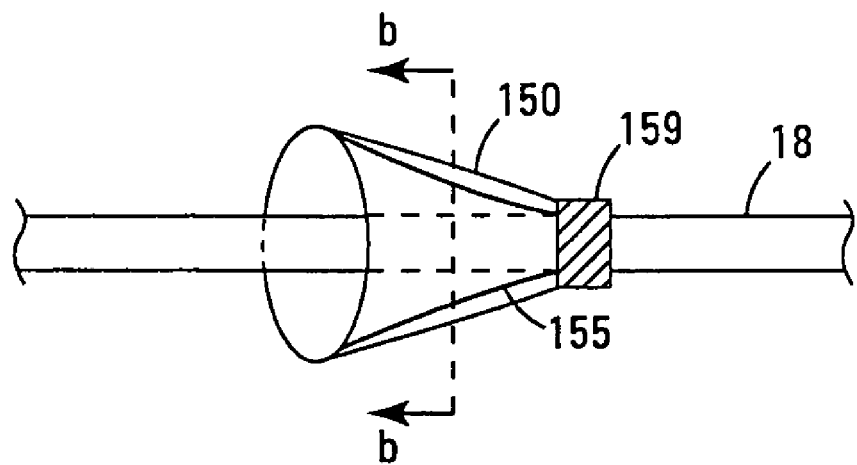
FIG. 15A is a side view of a further embodiment of the delivery catheter sealing cuff of this invention having reinforcing wires in the deployed configuration.
Figure 15B:
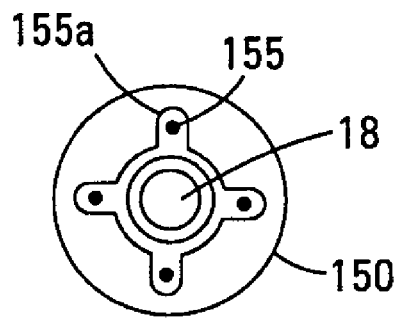
FIG. 15B is an end view showing the reinforcing wires disposed in channels of the sealing cuff.
Figure 15C:
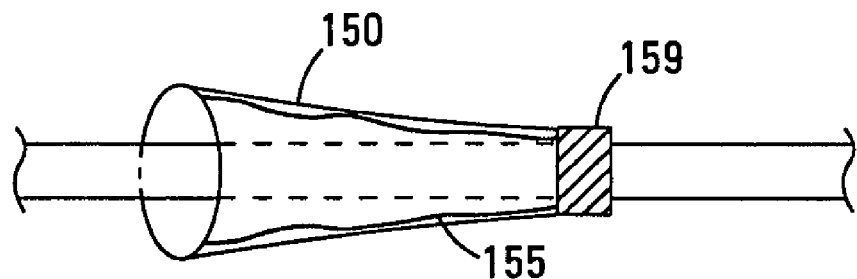
FIG. 15C is a side view of the sealing cuff in a delivery or removal configuration.

FIGS. 15A to 15C disclose an embodiment similar to that of FIGS. 14A to 14C except sealing cuff 150 has wires 155 disposed in channels in the sealing cuff. Sealing cuff 150 is attached to delivery catheter 18 by sliding element 159. The deployed configuration is shown in FIG. 15A. A cross-section along line b-b shows wires 155 in channels 155*a* in FIG. 15B. The wires bend to contact the catheter, as shown in FIG. 15C.

Figure 16:
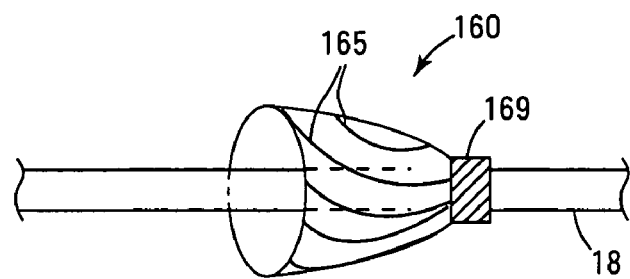
FIG. 16 is a side view of a further embodiment of the delivery catheter sealing cuff of this invention with helical wires.

FIG. 16 illustrates another embodiment where wires are used to stabilize the sealing cuff during delivery catheter advancement. Sealing cuff 160 comprises helical wires 165 which are embedded in the sealing cuff and in the sliding element. Sealing cuff 160 is affixed to sliding element 169 and disposed about catheter 18. When the sealing cuff is in its reduced diameter delivery configuration, the helical wires tend to straighten, wrapping more tightly around the catheter shaft, particularly in the vicinity of sliding element 169. Element 169 is slideable when the sealing cuff is in its deployed configuration, but is fixed when the sealing cuff is compressed, due to the action of the helical wires.

Figure 17:
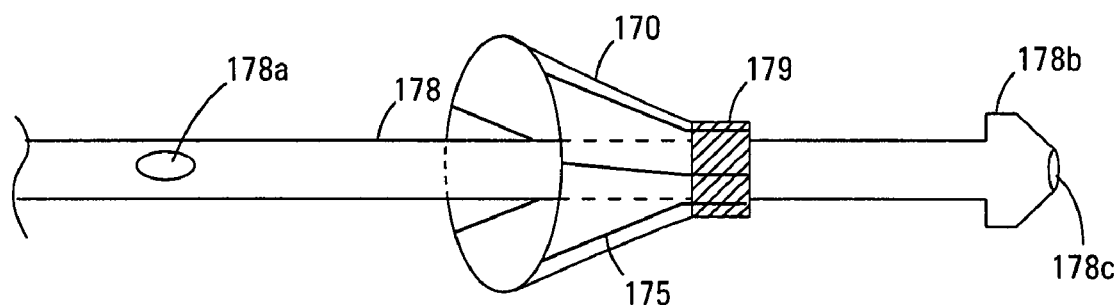
FIG. 17 is a perspective view of a further embodiment of the delivery catheter sealing cuff of this invention with lock wires.

FIG. 17 illustrates a further embodiment of a sealing cuff which includes frictional locking wires. Sealing cuff 170 is disposed about delivery catheter 178, which is provided with vent hole 178*a*. Vent hole 178*a* works in cooperation with distal opening 178*c* to provide a fluid path from a location distal to the sealing cuff to a location proximal to the sealing cuff during advancement of the delivery catheter through the guide catheter. As discussed previously this ensures that the catheter sealing cuff does not pull air into the guide catheter during advancement of the delivery catheter. It will be understood that similar vent holes can be provided with any of the embodiments disclosed herein. The sealing cuff is held on the catheter by sliding element 179, which is integral with the sealing cuff. Lock wires 175 extend the full length of the sealing cuff. In the delivery configuration the lock wires engage the catheter shaft. The distal end 178*b* of the catheter is enlarged so that the sealing cuff cannot slide off when the sealing cuff is in its deployed configuration and to allow for retrieval of the sealing cuff as previously described.

Figure 18:
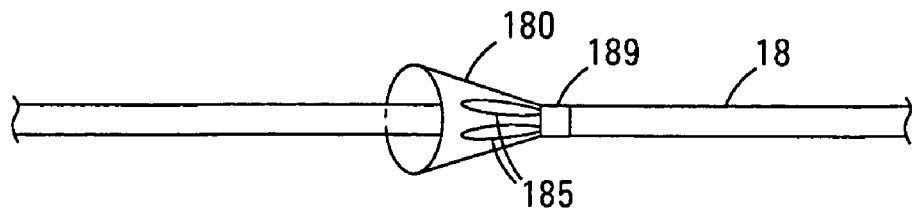
FIG. 18 is a side view of a further embodiment of the delivery catheter sealing cuff of this invention having reinforcing loops.

FIG. 18 illustrates a sealing cuff reinforced with looped petals of wire. There are no wire ends which could escape from the seal structure and potentially damage or perforate a vessel. Sealing cuff 180 is attached to the delivery catheter 18 by sliding element 189. Alternatively, element 189 can be fixed to the catheter. The sealing cuff has wire loops 185 covered with impermeable membrane. The wire loops also can be bent similar to the wires shown in FIG. 17 to provide a releasable lock in cooperation with sliding element 189, similar to that described for FIG. 17.

Figure 19A:
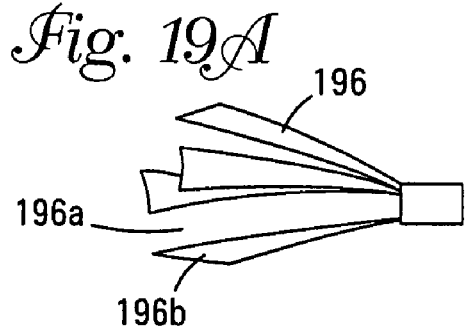
FIGS. 19A to 19C are perspective views of a further embodiment showing a wire frame, a polymeric membrane, and an assembled sealing cuff, respectively.
Figure 19B:
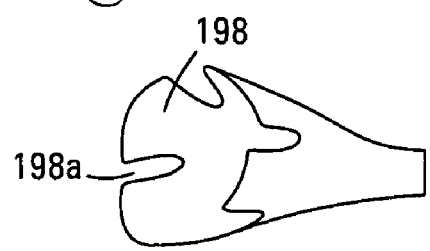
Figure 19C:
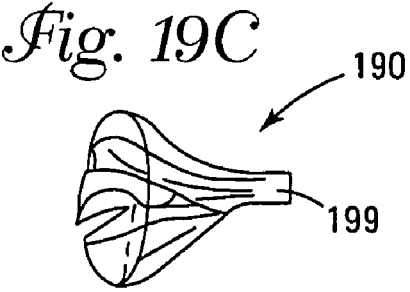

A further embodiment is disclosed in FIGS. 19A-19C. FIGS. 19A and 19*b* show a wire frame component and a flexible membrane component respectively which are joined to form the sealing cuff 190 shown in FIG. 19C. Wire frame 196 has a flower-like structure with gaps 196*a* and membrane covered gaps 196*b*. The impermeable polymeric membrane 198 is very flexible and has slots 198*a*, but has enough rigidity to seal against the wire frame without prolapsing between the gaps 196*a* in the wire frame. Membrane 198 fits inside the wire frame and is anchored at region 199 at/near the apex. During use, both frame and membrane will be anchored to the delivery catheter at region 199. Alternatively, they may be anchored to a slideable element or tube allowing the cuff to slide with respect to the delivery catheter.

When the catheter with sealing cuff 190 is advanced through a guide catheter or a vessel, fluid in vessel's lumen will bypass the sealing cuff by displacing membrane 198 away from frame 196, allowing fluid to pass through gaps 196*a* and past membrane 198. When sealing cuff 190 is stationary in a vessel, antegrade flow is stopped because antegrade flow pushes membrane 198 against frame 196, and slots 198*a* in the membrane align with membrane covered gaps 196*b*, effecting a seal. To assist the sealing effectiveness, membrane 198 may be biased to self-expand by forming membrane 198 from a stiff but thin material such as biaxially oriented nylon or polyester or similar materials, commonly used in the art to form angioplasty balloons.

Figure 20A:
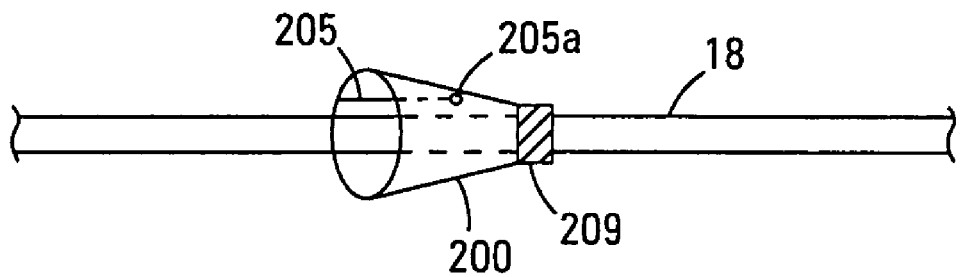
FIG. 20A is a side view of a further embodiment of the delivery catheter sealing cuff of this invention in the deployed configuration.
Figure 20B:
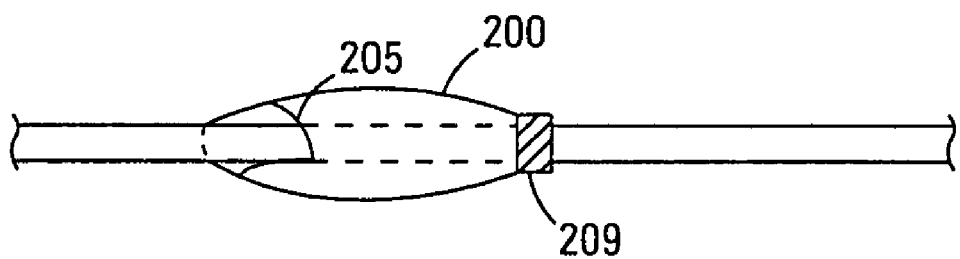
FIG. 20B is a side view and FIG. 20C is an end view of the sealing cuff of FIG. 20A in a collapsed configuration.
Figure 20C:
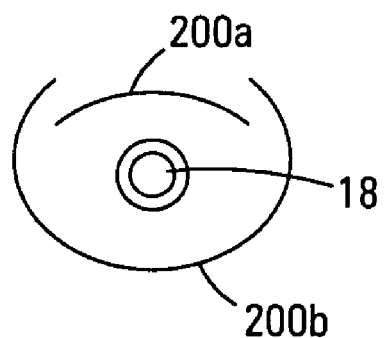

In another embodiment disclosed in FIGS. 20A to 20C the flexible membrane of the sealing cuff is configured in the shape of a duck bill valve. FIG. 20A shows a deployed configuration of sealing cuff 200 attached to slider element 209 and disposed about delivery catheter 18. Sealing cuff 200 has one or more slits 205 which divide sealing cuff 200 into portions 200*a* and 200*b*. A circular hole 205*a* may be provided to act as a stress reducer at the end of the slit. This prevents tearing of the polymeric membrane. Sealing cuff 200 is shown in its collapsed configuration in FIG. 20B and in end view in FIG. 20C. As best seen in FIG. 20C in its collapsed delivery configuration portions 200*a* and 200*b* overlap to permit fluid flow past the seal during delivery catheter advancement thereby preventing air from being sucked into the guide catheter. As seen in FIG. 20A, when deployed, portions 200*a* and 200*b* overlap to effect a seal and prevent distal blood flow.

The device and method of this invention is particularly useful during interventional procedures such as in cardiology, radiology, and neuroradiology procedures.

Although particular embodiments of the invention have been disclosed herein in detail, this has been done for the purposes of illustration only, and is not intended to be limiting with respect to the scope of the appended claims. It is contemplated that various substitutions, alterations, and modifications may be made to the embodiments of the invention described herein without departing from the spirit and scope of the invention as defined by the claims.

What is claimed is:

1. A method of deploying an embolic protection device carried on an elongate support member at a location distal to a treatment site in a vessel of a patient comprising:

providing a delivery catheter having a distal end and a lumen sized to slideably receive the elongate support member and embolic protection device, the delivery catheter having an elongate tubular shaft encircled by a sealing member, the sealing member being expandable from a delivery configuration to a deployed configuration, the sealing member being disposed on and carried by the elongate tubular shaft, and a distal end of the elongate tubular shaft being the distal end of the delivery catheter;

introducing a guide catheter into the vessel;

advancing the guide catheter through the vessel until a distal end of the guide catheter is at a desired location proximal of the treatment site;

advancing the delivery catheter containing the embolic protection device through the lumen of the guide catheter until the sealing member extends from the distal end of the guide catheter;

occluding the flow of blood through the vessel with the sealing member of the delivery catheter in the deployed configuration;

after blood flow has been occluded by the sealing member of the delivery catheter, advancing the distal end of the elongate tubular shaft of the delivery catheter through the vessel to a point distal to the treatment site and then advancing the embolic protection device to the location distal to the treatment site; and deploying the embolic protection device.

2. The method of claim 1 wherein in the step of providing a delivery catheter the sealing member is able to slide over a portion of the elongate tubular shaft, the sealing member having a proximal and a distal end, both the proximal and distal ends being slideable relative to the elongate tubular shaft, and after blood flow has been occluded, the elongate tubular shaft of the delivery catheter slides through the sealing member of the delivery catheter.

3. The method of claim 1 wherein the step of deploying the embolic protection device comprises deploying a filtration device.

4. The method of claim 1 wherein the step of deploying the embolic protection device comprises deploying an occlusive device.

5. The method of claim 4 wherein the occlusive device is a balloon.

6. The method of claim 1 wherein in the deployed configuration the sealing member is cone shaped having an apex pointed towards the distal end of the delivery catheter.

7. The method of claim 1 wherein in the deployed configuration the sealing member is bulb shaped.

8. The method of claim 1 wherein in the step of providing a delivery catheter the sealing member is self-expandable.

9. The method of claim 1 wherein when the sealing member of the delivery catheter is advanced through the lumen of the guide catheter, the sealing member is non-occlusive.

10. The method of claim 1 wherein when the sealing member of the delivery catheter is advanced through the lumen of the guide catheter, the sealing member is locked onto the elongate tubular shaft of the delivery catheter and when the distal end of the elongate tubular shaft of the delivery catheter is advanced through the vessel after blood flow has been occluded by the sealing member of the delivery catheter, the sealing member is slideable over a portion of the elongate tubular shaft and both the proximal and distal ends of the sealing member are slideable relative to the elongate tubular shaft.

11. A method of delivering an embolic protection device carried on an elongate support member to a location distal to a treatment site in a vessel of a patient comprising:

providing a delivery catheter having a distal end and a lumen sized to slideably receive the elongate support member and embolic protection device, the delivery catheter having an elongate tubular shaft encircled by a sealing member, the sealing member being expandable from a delivery configuration to a deployed configuration, the sealing member being disposed on and carried by the elongate tubular shaft, and a distal end of the elongate tubular shaft being the distal end of the delivery catheter;

introducing a guide catheter into the vessel;

advancing the guide catheter through the vessel until a distal end of the guide catheter is at a desired location proximal of the treatment site;

advancing the delivery catheter containing the embolic protection device through the lumen of the guide catheter until the sealing member extends from the distal end of the guide catheter;

occluding the flow of blood through the vessel with the sealing member of the delivery catheter in the deployed configuration; and after blood flow has been occluded by the sealing member of the delivery catheter, advancing the distal end of the elongate tubular shaft of the delivery catheter through the vessel to a point distal to the treatment site and then advancing the embolic protection device to the location distal to the treatment site.

12. The method of claim 11 wherein in the step of providing a delivery catheter the sealing member is able to slide over a portion of the elongate tubular shaft, the sealing member having a proximal and a distal end, both the proximal and distal ends being slideable relative to the elongate tubular shaft, and after blood flow has been occluded, the elongate tubular shaft of the delivery catheter slides through the sealing member of the delivery catheter.

13. The method of claim 11 wherein the embolic protection device is a filtration device.

14. The method of claim 11 wherein the embolic protection device is an occlusive device.

15. The method of claim 14 wherein the occlusive device is a balloon.

16. The method of claim 11 wherein in the deployed configuration the sealing member is cone shaped having an apex pointed towards the distal end of the delivery catheter.

17. The method of claim 11 wherein in the deployed configuration the sealing member is bulb shaped.

18. The method of claim 11 wherein in the step of providing a delivery catheter the sealing member is self-expandable.

19. The method of claim 11 wherein when the sealing member of the delivery catheter is advanced through the lumen of the guide catheter, the sealing member is non-occlusive.

20. The method of claim 11 wherein when the sealing member of the delivery catheter is advanced through the lumen of the guide catheter, the sealing member is locked onto the elongate tubular shaft of the delivery catheter and when the distal end of the elongate tubular shaft of the delivery catheter is advanced through the vessel after blood flow has been occluded by the sealing member of the delivery catheter, the sealing member is slideable over a portion of the elongate tubular shaft and both the proximal and distal ends of the sealing member are slideable relative to the elongate tubular shaft.

* * * * *